US010765666B2

(12) United States Patent
During

(10) Patent No.: US 10,765,666 B2
(45) Date of Patent: Sep. 8, 2020

(54) USE OF GABOXADOL FOR THE TREATMENT OF TOURETTE SYNDROME, TICS AND STUTTERING

(71) Applicant: Ovid Therapeutics Inc., New York, NY (US)

(72) Inventor: Matthew During, Weston, CT (US)

(73) Assignee: OVID THERAPEUTICS INC, New York, NY (US)

( * ) Notice: Subject to any disclaimer, the term of this patent is extended or adjusted under 35 U.S.C. 154(b) by 0 days.

(21) Appl. No.: 16/577,084

(22) Filed: Sep. 20, 2019

(65) Prior Publication Data

US 2020/0093806 A1    Mar. 26, 2020

Related U.S. Application Data

(60) Provisional application No. 62/733,730, filed on Sep. 20, 2018.

(51) Int. Cl.
*A61K 31/437* (2006.01)
*A61P 25/14* (2006.01)

(52) U.S. Cl.
CPC ........... *A61K 31/437* (2013.01); *A61P 25/14* (2018.01)

(58) Field of Classification Search
CPC .................... A61K 31/437; A61K 31/4355
USPC ........................................................ 514/302
See application file for complete search history.

(56) References Cited

U.S. PATENT DOCUMENTS

| | | | |
|---|---|---|---|
| 2,830,083 A | 4/1958 | Gilbert et al. | |
| 4,084,000 A | 4/1978 | Fuxe | |
| 4,278,676 A | 7/1981 | Krogsgaard-LarsenPovl | |
| 4,353,910 A | 10/1982 | Perregaard | |
| 4,362,731 A | 12/1982 | Hill | |
| 5,929,065 A | 7/1999 | Lancel | |
| 8,569,355 B2 | 10/2013 | Laudon et al. | |
| 9,339,495 B2 | 5/2016 | During | |
| 9,351,968 B1 | 5/2016 | During | |
| 9,399,034 B1 | 7/2016 | During et al. | |
| 9,446,028 B2 | 9/2016 | During | |
| 9,682,069 B2 | 6/2017 | During | |
| 9,717,716 B2 | 8/2017 | During et al. | |
| 9,744,159 B2 | 8/2017 | During | |
| 9,801,864 B2 | 10/2017 | During | |
| 9,913,833 B2 | 3/2018 | During | |
| 10,071,083 B2 | 9/2018 | During | |
| 10,188,635 B2 | 1/2019 | During | |
| 2002/0165217 A1 | 11/2002 | Howard | |
| 2004/0024038 A1 | 2/2004 | Ebert et al. | |
| 2004/0087576 A1* | 5/2004 | Haracz ............... | A61K 31/5513 514/221 |
| 2005/0137222 A1 | 6/2005 | Ebert et al. | |
| 2005/0215521 A1 | 9/2005 | Lalji et al. | |
| 2007/0032553 A1 | 2/2007 | McKernan et al. | |
| 2007/0112017 A1 | 5/2007 | Barlow et al. | |
| 2007/0259912 A1 | 11/2007 | Cooper | |
| 2008/0207601 A1 | 8/2008 | Sabnani | |
| 2008/0269278 A1 | 10/2008 | Lundahl et al. | |
| 2009/0048288 A1 | 2/2009 | Ebert et al. | |
| 2009/0143335 A1 | 6/2009 | Larsen et al. | |
| 2009/0203731 A1 | 8/2009 | Sanchez et al. | |
| 2009/0269795 A1 | 10/2009 | Smith | |
| 2010/0029770 A1 | 2/2010 | Roberts et al. | |
| 2010/0093787 A1 | 4/2010 | Lundahl et al. | |
| 2011/0046090 A1 | 2/2011 | Barlow et al. | |
| 2012/0035207 A1 | 2/2012 | McKernan et al. | |
| 2012/0302554 A1 | 11/2012 | Knipper-Breer et al. | |
| 2013/0251671 A1 | 9/2013 | Kaufman et al. | |
| 2015/0164911 A1 | 6/2015 | Chipkin et al. | |
| 2015/0313913 A1 | 11/2015 | Catterall et al. | |
| 2015/0352085 A1 | 12/2015 | During | |
| 2016/0038469 A1 | 2/2016 | During | |
| 2016/0228418 A1 | 8/2016 | During | |
| 2017/0014392 A1 | 1/2017 | During | |
| 2017/0014393 A1 | 1/2017 | During | |
| 2017/0042863 A1 | 2/2017 | During et al. | |
| 2017/0087133 A1 | 3/2017 | During | |
| 2017/0348232 A1 | 12/2017 | During | |
| 2018/0036298 A1 | 2/2018 | During | |
| 2018/0042903 A1 | 2/2018 | During | |
| 2018/0098974 A1 | 4/2018 | During | |
| 2018/0235942 A1 | 8/2018 | During et al. | |
| 2018/0344708 A1 | 12/2018 | During | |

FOREIGN PATENT DOCUMENTS

| | | |
|---|---|---|
| DE | 102005020882 A1 | 11/2006 |
| EP | 0000338 A2 | 1/1979 |
| EP | 0840601 B1 | 10/2001 |
| EP | 1337247 B1 | 8/2006 |
| EP | 1641456 B1 | 3/2010 |
| EP | 3372229 A1 | 9/2018 |
| GB | 2410434 A | 8/2005 |
| JP | 2012501301 A | 1/2012 |
| WO | 97/02813 A1 | 1/1997 |
| WO | 2005023256 A1 | 3/2005 |
| WO | 2005058313 A1 | 6/2005 |
| WO | 2005094820 A1 | 10/2005 |
| WO | 2006013397 A1 | 2/2006 |

(Continued)

OTHER PUBLICATIONS

Berman et al., "Mouse Models of Fragile X-Associated Tremor Ataxia," J. Investig Med., Dec. 2009, vol. 57, No. 8, pp. 837-841. (10 pages).

(Continued)

*Primary Examiner* — Charanjit Aulakh
(74) *Attorney, Agent, or Firm* — Carter, DeLuca & Farrell LLP

(57) ABSTRACT

Treatment of Tourette syndrome using gaboxadol or a pharmaceutically acceptable salt thereof is provided. Treatment of tics using gaboxadol or a pharmaceutically acceptable salt thereof is provided. Treatment of stuttering using gaboxadol or a pharmaceutically acceptable salt thereof is provided. Therapeutic compositions that may be used to improve one or more symptoms of Tourette syndrome are provided. Therapeutic compositions that may be used to improve one or more symptoms of tics are provided. Also provided are therapeutic compositions that may be used to improve one or more symptoms of stuttering.

20 Claims, 1 Drawing Sheet

(56) References Cited

FOREIGN PATENT DOCUMENTS

| WO | 2009056146 A1 | 5/2009 | |
| --- | --- | --- | --- |
| WO | WO 2010/015037 A1 * | 2/2010 | ......... A61K 31/4184 |
| WO | 2014123909 A1 | 8/2014 | |
| WO | 2017015049 A1 | 1/2017 | |
| WO | 2017027249 A1 | 2/2017 | |

OTHER PUBLICATIONS

Entezam et al.., "Regional FMRP deficits and large repeat expansions into the full mutation range in a new Fragile X premutation mouse model," Gene, 2007, vol. 395, No. 1-2, pp. 125-134 (18 pages).

Tassone et al., "Elevated Levels of FMR1 mRNA in Carrier Males: A New Mechanism of Involvement in the Fragile X Syndrome," Am. J. Hum. Genet., 2000, vol. 66; pp. 6-15.

Boyle et al., "Next-day residual effects of gaboxadol and flurazepam administered at bedtime: a randomized double-blind study in healthy elderly subjects," Human Psychopharmacology, 2009, vol. 24, pp. 61-71.

Chaturvedi et al., "Fast Dissolving Films: A Review," Current Drug Delivery, 2011, vol. 8; pp. 373-380.

Ciper and Bodmeier, "Preparation and characterization of novel fast disintegrating capsules (Fastcaps) for administration in the oral cavity," Science Direct, International Journal of Pharmaceutics, 2005, vol. 303; pp. 62-71.

Boateng et al., "Characterisation of freeze-dried wafers and solvent evaporated films as potential drug delivery systems to mucosal surfaces," International Journal of Pharmaceutics, vol. 389, Issues 1-2, Apr. 15, 2010, pp. 24-31.

Journal of Labelled Compounds and Radiopharmaceuticals, 1982, vol. 19, No. 5; pp. 689-702.

Sametsky et al., "Enhanced GABAA-Mediated Tonic Inhibition in Auditory Thalamus of Rats with Behavioral Evidence of Tinnitus", The Journal of Neuroscience, vol. 35, No. 25, Jun. 24, 2015; pp. 9369-9380.

Richardson et al., "Targeting Inhibitory Neurotransmission in Tinnitus", Elsevier, SciVerse ScienceDirect, Brain Research 1485, Feb. 2012; pp. 77-87.

International Search Report and Written Opinion, dated Oct. 31, 2017, corresponding to International Application No. PCT/US17/46256; 10 total pages.

Chilean Office Action dated Feb. 13, 2019, corresponding to Chilean Application No. 201800142; 7 pages.

International Search Report and the Written Opinion of the International Searching Authority, dated Jul. 1, 2019, corresponding to counterpart International Application No. PCT/US19/26218; 10 total pages.

International Search Report and Written Opinion of the International Searching Authority, dated Apr. 24, 2018, corresponding to International Application No. PCT/U5218/16602; 15 total pages.

International Search Report and Written Opinion, dated Oct. 4, 2016, corresponding to International Application No. PCT/US16/50702; 9 total pages.

International Search Report and Written Opinion of the International Searching Authority, dated Jul. 18, 2017, corresponding to International Application No. PCT/U517/34443; 5 total pages.

Loescher, W., "Development of Tolerance to the Anticonvulsant Effect of GABA-mimetic Drugs in Animal Models of Seizure States in Tolerance to Beneficial and Adverse Effects of Antiepileptic Drugs," Koella et al. (eds.), pp. 37-45 (1986).

Petersen et al., "THIP: A Single Blind Controlled Trial in Patients with Epilepsy," Acta Neurol. Scand. 67; pp. 114-117 (1983).

Notification Concerning Transmittal of International Preliminary Report on Patentability, dated Jun. 6, 2019, International Preliminary Report on Patentability dated May 28, 2019, corresponding to counterpart International Application No. PCT/US2017/062685 and Written Opinion of the International Searching Authority corresponding to counterpart Application No. PCT/US2017/062685; 11 total pages.

Bahi-Buisson et al., "The three stages of epilepsy in patients with CDKL5 mutations", Epilepsia, vol. 49, No. 6; 2008; pp. 1027-1037.

Cheng et al., "Inducing Anesthesia with a GABA Analog, THIP,", Anesthesiology, vol. 63, No. 2, Aug. 1985; pp. 147-151.

Ebert et al., "Treating Insomnia: Current and Investigational Pharmacological Approaches," Pharmacology & Therapeutics, vol. 112, 2006; pp. 612-629.

Walsh et al.,., "The Selective Extrasynaptic GABAA Agonist, Gaboxadol, Improves Traditional Hypnotic Efficacy Measures and Enhances Slow Wave Activity in a Model of Transient Insomnia," Sleep, vol. 30, No. 5, 2007; pp. 593-602.

Stephanie Saul, "Merck Cancels Work on a New Insomnia Medication," The New York Times, Mar. 29, 2007; 2 pages.

Ransdell Pierson, Update 2—Merck, Lundbeck scrap insomnia drug after trials, Rueters, (Dow Jones); Mar. 26, 2007; 2 pages.

James K. Walsh, Ph.D., "Enhancement of Slow Wave Sleep: Implications for Insomnia," Journal of Clinical Sleep Medicine, Supplement to vol. 5, No. 2, (2009); pp. 827-832.

International Search Report and Written Opinion of the International Searching Authority, dated Aug. 26, 2015, corresponding to International Application No. PCT/US15/34018; 12 total pages.

Walter, Alexander, "Sleep: Gaboxadol Enhances Slow Wave Sleep," Perelman, School of Medicine, Jun. 22, 2006; 3 pages.

Brown et al., "Pharmacological Characterization of a Novel Cell Line Expressing Human α4β3δ GABAA Receptors," British Journal of Pharmacology, vol. 136, No. 7, 2002; pp. 965-974.

Deacon et al., "Effect of Short-Term Treatment with Gaboxadol on Sleep Maintenance and Initiation in Patients with Primary Insomnia," Sleep, vol. 30, No. 3, 2007; pp. 281-287.

Faulhaber et al., "The GABAA Agonist THIP Produces Slow Wave Sleep and Reduces Spindling Activity in NREM Sleep in Humans," Psychopharmacology, vol. 130, 1997; pp. 285-291.

Gaboxadol, from Wikipedia, the free encyclopedia,http://en.wikipedia.org/wiki/Gaboxadol, 2014; 2 pages.

Gaboxadol, Investigational Agent—Drug Development Technology, http://www.drugdevelopment-technology.com/projects/gaboxadol—2014; 3 pages.

Gaboxadol, Bluelight, http://www.bluelight.org/vb/threads/370965-Gaboxadol—(2014); 1 page.

Glykys et al., "The Main Source of Ambient GABA Responsible for Tonic Inhibition in the Mouse Hippocampus," J Physiol, vol. 582, No. 3, 2007; pp. 1163-1178.

Hajak et al., "A 2-week Efficacy and Safety Study of Gaboxadol and Zolpidem Using Electronic Diaries in Primary Insomnia Outpatients," Sleep Medicine, vol. 10, 2009; pp. 705-712.

Jennum et al., "Sleep Disorders in Neurodegenerative Disorders and Stroke," European Handbook of Neurological Management, vol. 1, 2nd Edition, Chapter 39, Section 6—Sleep Disorders, (Ed. Gilhus et al.) Blackwell Publishing Ltd. 2011; pp. 529-543.

Jonas et al., "Neural Inhibition,", Scholarpedia—http://www.scholarpedia.org/article/Neural.sub.-inhibition-—(2014); 10 pages.

Lancel et al., "The GABAA Agonist THIP (Gaboxadol) Increases Non-REM Sleep and Enhances Delta Activity in the Rat," Sleep and Rhythms, NeuroReport, Rapid Science Publishers, vol. 7, No. 13; Sep. 1996; pp. 2241-2245.

Marike Lancel, "The GABAA Agonist THIP Increases Non-REM Sleep and Enhances Non-REM Sleep-Specific Delta Activity in the Rat During the Dark Period," Sleep, vol. 20, No. 12, American Sleep Disorders Association and Sleep Research Society (1997); pp. 1099-1104.

Marike Lancel, "Role of GABAA Receptors in the Regulation of Sleep: Initial Sleep Responses to Peripherally Administered Modulators and Agonists," Sleep, vol. 22, No. 1, (1999); pp. 33-42.

Lancel et al., "Effect of the GABAA Agonist Gaboxadol on Nocturnal Sleep and Hormone Secretion in Healthy Elderly Subjects," Am J. Physiol Endoctrinol Metab, vol. 281; (2001), pp. E130-E137.

Larsen et al.,—Research Paper—"Intestinal Gaboxadol Absorption via PAT1 (SLC36A1): Modified Absorption in vivo Following Co-administration of L-tryptophan," British Journal of Pharmacology (BJP), vol. 157, (2009); pp. 1380-1389.

Lundahl et al., "Short-term Treatment with Gaboxadol Improves Sleep Maintenance and Enhances Slow Wave Sleep in Adult Patients with Primary Insomnia," Psychopharmacology, vol. 195, (2007); pp. 139-146.

(56) References Cited

OTHER PUBLICATIONS

Mathias et al., "The GABAA Agonist Gaboxadol Improves the Quality of Post-Nap Sleep," Psychopharmacology, vol. 157 (2001); pp. 299-304.
Mathias et al., "Effect of Repeated Gaboxadol Administration on Night Sleep and Next-Day Performance in Healthy Elderly Subjects," Neuropsychopharmacology, vol. 30, (2005) pp. 833-841.
Natural Patterns of Sleep—Healthy Sleep—http://healthysleep.med.harvard.edu/healthy/science/what/sleep-pat-terns-rem-nrem (2007); 3 pages.
Olmos-Serrano et al, "The GABAA Receptor Agonist THIP Ameliorates Specific Behavioral Deficits in the Mouse Model of Fragile X Syndrome," Developmental Neuroscience, vol. 33, Fragile X Syndrome/Review, (2011), pp. 395-403.
Vardya et al., "Positive Modulation of δ-Subunit Containing GABAA Receptors in Mouse neurons" Neuropharmacology, vol. 63; 2012; pp. 469-479.
International Search Report and Written Opinion of the International Searching Authority, dated Sep. 27, 2016, corresponding to International Application No. PCT/US16/42238; 8 total pages.
Egawa et al., "Pathophysiological power of improper tonic GABA(A) conductances in mature and immature models." Frontiers in Neural Circuits, Oct. 24, 2013, vol. 7, Article 170; pp. 1-15.
PCT Notice concerning Transmittal of International Preliminary Report on Patentability (Chapter I of the Patent Cooperation Treaty), International Preliminary Report on Patentability and Written Opinion of the International Searching Authority, dated Feb. 1, 2018, corresponding to International Application No. PCT/US2016/042238; 8 total pages.
European Search Report dated Feb. 13, 2019, corresponding to European Application No. 16828266.3; 11 pages.
Peixoto et al., "Effects of gabaergic drugs on reserpine-induced oral dyskinesia," Behavioural Brain Research, vol. 160, (2005); pp. 51-59.
Reagan-Shaw et al., "Dose translation from animal to human studies revisited", FASEB J, vol. 22, No. 3, Oct. 17, 2007; pp. 659-661.
International Search Report and Written Opinion of the International Searching Authority, dated Aug. 14, 2015, corresponding to International Application No. PCT/US2015/029155; 19 total pages.
Oakley et al., "Synergistic GABA-Enhancing Therapy against Seizures in a Mouse Model of Dravet Syndrome," The Journal of Pharmacology and Experimental Therapeutics, vol. 345, May 2013; pp. 215-224.
Nagar et al., "Orally disintegrating tablets: formulation, preparation techniques and evaluation", Journal of Applied Pharmaceutical Science, vol. 01, No. 04, 2011; pp. 35-45.
Gupta Nitan Bharti et al., "Pulsatile Drug Delivery as Modified Release Dosage Form: A Review", Journal of Drug Delivery & Therapeutics, vol. 2, No. 6, 2012; pp. 102-110.
Reddy et al., "Review On: Pulsatile Drug Delivery Systems", Journal of Pharmaceutical Sciences and Research, (ISSN: 0975-1459), vol. 1, No. 4, 2009; pp. 109-115.
The United States Pharmacopeia (USP) disintegration test method set forth at section 701 Disintegration, Revision Bulletin Official Aug. 1, 2008; pp. 1-3.
Bharawaj et al., "Orally Disintegrating Tablets: A Review", Drug Invention Today, vol. 2, No. 1, (ISSN: 0975-7619), 2010; pp. 81-88.
Boyle et al., "Tolerability, pharmacokinetics and night-time effects on postural sway and critical flicker fusion of gaboxadol and zolpidem in elderly subjects," British Journal of Clinical Pharmacology, 2008, vol. 67, No. 2; pp. 180-190.
Guidance for Industry, Orally Disintegrating Tablets, United States Department of Health and Human Services, Food and Drug Administration, Center for Drug Evaluation and Research (CDER), Dec. 2008, Chemistry, pp. 1-8.
Yapar et alo., "Orally Disintegrating Tablets: An Overview," Journal of Applied Pharmaceutical Science, Feb. 2014, vol. 4, No. 02, pp. 118-125.
Fu et al., "Drug Release Kinetics and Transport Mechanisms of Non-degradable and Degradable Polymeric Delivery Systems," NIH Public Access, Author Manuscript, National Institute of Health, Expert Opin Drug Deliv., Apr. 2010; vol. 7, No. 4 (pp. 429-444) 28 pages.
Cao et al., "Clustered burst firing in FMR1 premutation hippocampal neurons: amelioration with allopregnanolone," Human Molecular Genetics, 2012, vol. 21, No. 13, pp. 2923-2935.
Kesisoglou et al., "Utility of PBPK Absorption Modeling to Guide Modified Release Formulation Development of Gaboxadol, a Highly Soluble Compound with Region-Dependent Absorption," Research Article—Pharmaceutics, Drug Delivery and Pharmaceutical Technology, Aug. 19, 2015; Journal of Pharmaceutical Sciences, vol. 105 (2016); pp. 722-728 (7 pages).
Bacalman et al., "Psychiatric Phenotype of the Fragile X-Associated Tremor/Ataxia Syndrome (FXTAS) in Males: Newly Described Fronto-Subcortical Dementia," J. Clinical Psychiatry, 2006, vol. 67; pp. 87-94.
Jacquemont et al., "Fragile-X syndrome and fragile X-associated tremor/ataxia syndrome: two faces of FMR1," Neurology, The Lancet, vol. 6, Jan. 2007, pp. 45-55.
International Search Report and Written Opinion of the International Searching Authority, dated Jan. 31, 2020, corresponding to counterpart International Application No. PCT/US2019/052085; 13 total pages.
Da Cruz, "Verbal Repetitions and Echolalia in Alzheimer's Discourse," Clinical Linguistics & Phonetics, vol. 24, No. 11; Nov. 2010, pp. 848-858.

* cited by examiner

USE OF GABOXADOL FOR THE TREATMENT OF TOURETTE SYNDROME, TICS AND STUTTERING

CROSS-REFERENCE TO RELATED APPLICATION

This application claims benefit and priority to U.S. Provisional Application No. 62/733,730, filed Sep. 20, 2018, which is incorporated herein by reference in its entirety.

TECHNICAL FIELD

Treatment of Tourette syndrome, tics and stuttering.

BACKGROUND

Tourette syndrome (TS) is a neurological disorder characterized by repetitive, stereotyped, involuntary movements and vocalizations called tics. According to the National Institute of Neurological Disorders and Stroke, the first symptoms of TS are almost always noticed in childhood, usually appearing between the ages of 3 and 12. Tics may be classified as either simple or complex. Simple motor tics are sudden, brief, repetitive movements that involve a limited number of muscle groups. Some of the more common simple tics include eye blinking and other eye movements, facial grimacing, shoulder shrugging, and head or shoulder jerking. Simple vocalizations might include repetitive throat-clearing, sniffing, or grunting sounds. Complex tics are distinct, coordinated patterns of movements involving several muscle groups. Complex motor tics might include facial grimacing combined with a head twist and a shoulder shrug. Other complex motor tics may actually appear purposeful, including sniffing or touching objects, hopping, jumping, bending, or twisting. Simple vocal tics may include throat-clearing, sniffing/snorting, grunting, or barking. More complex vocal tics include words or phrases. Perhaps the most dramatic and disabling tics are those that result in self-harm such as punching oneself, or vocal tics including coprolalia (uttering swear words) or echolalia (repeating the words or phrases of others). Medications may be administered to control some symptoms of TS. For example, typical and atypical neuroleptic agents including risperidone, ziprasidone, haloperidol, pimozide and fluphenazine may be utilized but can have long-term and short-term adverse effects. Antihypertensive agents such as clonidine and guanfacine are also used to treat tics.

According to the National Institute on Deafness and Other Communication Disorders (NIDCD) stuttering is a speech disorder characterized by repetition of sounds, syllables, or words; prolongation of sounds; and interruptions in speech known as blocks. An individual who stutters exactly knows what he or she would like to say but has trouble producing a normal flow of speech. These speech disruptions may be accompanied by struggle behaviors, such as rapid eye blinks or tremors of the lips. Stuttering can make it difficult to communicate with other people, which often affects a person's quality of life and interpersonal relationships. Stuttering can also negatively influence job performance and opportunities, and treatment can come at a high financial cost. Symptoms of stuttering can vary significantly throughout a person's day.

Stuttering affects people of all ages. It occurs most often in children between the ages of 2 and 6 as they are developing their language skills. Approximately 5 to 10 percent of all children will stutter for some period in their life, lasting from a few weeks to several years. Approximately 75 percent of children recover from stuttering. For the remaining 25 percent who continue to stutter, stuttering can persist as a lifelong communication disorder.

Stuttering is commonly grouped into two types termed developmental and neurogenic. Developmental stuttering occurs in young children while they are still learning speech and language skills. It is the most common form of stuttering. Most scientists and clinicians believe that developmental stuttering stems from complex interactions of multiple factors. Recent brain imaging studies have shown consistent differences in those who stutter compared to nonstuttering peers. Developmental stuttering may also run in families and research has shown that genetic factors contribute to this type of stuttering. Neurogenic stuttering may occur after a stroke, head trauma, or other type of brain injury. With neurogenic stuttering, the brain has difficulty coordinating the different brain regions involved in speaking, resulting in problems in production of clear, fluent speech.

The U.S. Food and Drug Administration has not approved any drug for the treatment of stuttering. However, some drugs that are approved to treat other health problems—such as epilepsy, anxiety, or depression—have been used to treat stuttering. These drugs often have side effects that make them difficult to use over a long period of time.

Gaboxadol (4,5,6,7-tetrahydroisoxazolo [5,4-c]pyridine-3-ol) (THIP)) is described in EP Patent No. 0000338 and in EP Patent No. 0840601, U.S. Pat. Nos. 4,278,676, 4,362,731, 4,353,910, and WO 2005/094820. Gaboxadol is a selective $GABA_A$ receptor agonist with a preference for δ-subunit containing $GABA_A$ receptors. In the early 1980s gaboxadol was the subject of a series of pilot studies that tested its efficacy as an analgesic and anxiolytic, as well as a treatment for tardive dyskinesia, Huntington's disease, Alzheimer's disease, and spasticity. In the 1990s gaboxadol moved into late stage development for the treatment of insomnia. The development was discontinued after the compound failed to show significant effects in sleep onset and sleep maintenance in a three-month efficacy study. Additionally, patients with a history of drug abuse who received gaboxadol experienced a steep increase in psychiatric adverse events.

SUMMARY

Methods of treating Tourette syndrome include administering gaboxadol or a pharmaceutically acceptable salt thereof to a patient in need thereof to provide improvement in one or more symptoms of the Tourette syndrome. Pharmaceutical compositions including gaboxadol or a pharmaceutically acceptable salt thereof are provided for use in treating Tourette syndrome. Methods of treating Tourette syndrome include administering a pharmaceutical composition including gaboxadol or a pharmaceutically acceptable salt thereof to a patient in need thereof. In embodiments, methods of treating Tourette syndrome include administering gaboxadol or a pharmaceutically acceptable salt thereof to a patient in need thereof to provide improvement in symptoms of the Tourette syndrome in the patient a day after administration of the gaboxadol or a pharmaceutically acceptable salt thereof.

Methods of treating Tourette syndrome described herein include administering to a patient in need thereof about 0.05 mg to about 30 mg gaboxadol or a pharmaceutically acceptable salt thereof wherein the method provides improvement in Tourette syndrome. Methods of treating Tourette syndrome described herein include administering to a patient in need thereof a composition including about 0.05 mg to about 30 mg gaboxadol or a pharmaceutically acceptable salt thereof wherein the composition provides improvement in Tourette syndrome. Methods of treating Tourette syndrome described herein include administering to a patient in need thereof about 0.05 mg to about 30 mg gaboxadol or a pharmaceutically acceptable salt thereof wherein the method provides improvement in one or more symptoms of Tourette syndrome. Methods of treating Tourette syndrome described herein include administering to a patient in need thereof a composition including about 0.05 mg to about 30 mg gaboxadol or a pharmaceutically acceptable salt thereof wherein the composition provides improvement in one or more symptoms of Tourette syndrome. Methods of treating Tourette syndrome described herein include administering to a patient in need thereof about 0.05 mg to about 30 mg gaboxadol or a pharmaceutically acceptable salt thereof wherein the method provides improvement in Tourette syndrome the next day. Methods of treating Tourette syndrome described herein include administering to a patient in need thereof a composition including about 0.05 mg to about 30 mg gaboxadol or a pharmaceutically acceptable salt thereof wherein the composition provides improvement in Tourette syndrome the next day. Methods of treating Tourette syndrome described herein include administering to a patient in need thereof about 0.05 mg to about 30 mg gaboxadol or a pharmaceutically acceptable salt thereof wherein the method provides improvement in the patient for more than 6 hours after administration to the patient. Methods of treating Tourette syndrome described herein include administering to a patient in need thereof a composition including about 0.05 mg to about 30 mg gaboxadol or a pharmaceutically acceptable salt thereof wherein the composition provides improvement in the patient for more than 6 hours after administration to the patient. Methods of treating Tourette syndrome are described herein which include administering to a patient in need thereof gaboxadol or a pharmaceutically acceptable salt thereof wherein the method provides an in vivo plasma profile including a $C_{max}$ less than about 400 ng/ml and wherein the method provides improvement in the patient for more than 6 hours after administration of the gaboxadol or a pharmaceutically acceptable salt thereof. Methods of treating Tourette syndrome are described herein which include administering to a patient in need thereof a composition including gaboxadol or a pharmaceutically acceptable salt thereof wherein the composition provides an in vivo plasma profile including a $C_{max}$ less than about 400 ng/ml and wherein the method provides improvement in the patient for more than 6 hours after administration of the gaboxadol or a pharmaceutically acceptable salt thereof. Methods of treating Tourette syndrome are described herein which include administering to a patient in need thereof gaboxadol or a pharmaceutically acceptable salt thereof wherein the method provides an in vivo plasma profile comprising a $AUC_{6-12}$ of less than about 900 ng·hr/ml and wherein the method provides improvement in the patient for more than 6 hours after administration of the gaboxadol or a pharmaceutically acceptable salt thereof. Methods of treating Tourette syndrome are described herein which include administering to a patient in need thereof a composition including gaboxadol or a pharmaceutically acceptable salt thereof wherein the composition provides an in vivo plasma profile comprising a $AUC_{6-12}$ of less than about 900 ng·hr/ml and wherein the method provides improvement in the patient for more than 6 hours after administration of the gaboxadol or a pharmaceutically acceptable salt thereof. Methods of treating Tourette syndrome are described herein which include administering to a patient in need thereof a first pharmaceutical composition including gaboxadol or a pharmaceutically acceptable salt thereof and a second pharmaceutical composition including gaboxadol or a pharmaceutically acceptable salt thereof wherein the second pharmaceutical composition provides an in vivo plasma profile having a mean $AUC_{0-\infty}$ of at least 20% less than the first pharmaceutical composition. Methods of treating Tourette syndrome are described herein which include administering to a patient in need thereof about 0.05 mg to about 30 mg gaboxadol or a pharmaceutically acceptable salt thereof in combination with a medicament selected from the group consisting of atypical neuroleptic agent and antihypertensive agent wherein the method provides improvement in Tourette syndrome. Methods of treating Tourette syndrome are described herein which include administering to a patient in need thereof a composition including about 0.05 mg to about 30 mg gaboxadol or a pharmaceutically acceptable salt thereof in combination with a medicament selected from the group consisting of atypical neuroleptic agent and antihypertensive agent wherein the composition provides improvement in Tourette syndrome.

Methods of treating tics include administering gaboxadol or a pharmaceutically acceptable salt thereof to a patient in need thereof to provide improvement in one or more tic symptoms. Pharmaceutical compositions including gaboxadol or a pharmaceutically acceptable salt thereof are provided for use in treating tics. Methods of treating tics include administering a pharmaceutical composition including gaboxadol or a pharmaceutically acceptable salt thereof to a patient in need thereof. In embodiments, methods of treating tics include administering gaboxadol or a pharmaceutically acceptable salt thereof to a patient in need thereof to provide improvement in tic symptoms in the patient a day after administration of the gaboxadol or a pharmaceutically acceptable salt thereof. In embodiments, the tics are not associated with TS.

Methods of treating tics described herein include administering to a patient in need thereof about 0.05 mg to about 30 mg gaboxadol or a pharmaceutically acceptable salt thereof wherein the method provides improvement in the tics. Methods of treating tics described herein include administering to a patient in need thereof a composition including about 0.05 mg to about 30 mg gaboxadol or a pharmaceutically acceptable salt thereof wherein the composition provides improvement in the tics. Methods of treating tics described herein include administering to a patient in need thereof about 0.05 mg to about 30 mg gaboxadol or a pharmaceutically acceptable salt thereof wherein the method provides improvement in one or more tic symptoms. Methods of treating tics described herein include administering to a patient in need thereof a composition including about 0.05 mg to about 30 mg gaboxadol or a pharmaceutically acceptable salt thereof wherein the composition provides improvement in one or more tic symptoms. Methods of treating tics described herein include administering to a patient in need thereof about 0.05 mg to about 30 mg gaboxadol or a pharmaceutically acceptable salt thereof wherein the method provides improvement in the tics the next day. Methods of treating tics described herein include administering to a patient in need thereof a composition including about 0.05 mg to about 30 mg gaboxadol or a pharmaceutically acceptable salt thereof wherein the composition provides improvement in the tics the next day. Methods of treating tics described herein include administering to a patient in need thereof about 0.05 mg to about 30 mg gaboxadol or a pharmaceutically acceptable salt thereof wherein the method provides improvement in the patient for more than 6 hours after administration to the patient. Methods of treating tics described herein include administering to a patient in need thereof a composition including about 0.05 mg to about 30 mg gaboxadol or a pharmaceutically acceptable salt thereof wherein the composition provides improvement in the patient for more than 6 hours after administration to the patient. Methods of treating tics are described herein which include administering to a patient in need thereof gaboxadol or a pharmaceutically acceptable salt thereof wherein the method provides an in vivo plasma profile including a $C_{max}$ less than about 400 ng/ml and wherein the method provides improvement in the patient for more than 6 hours after administration of the gaboxadol or a pharmaceutically acceptable salt thereof. Methods of treating tics are described herein which include administering to a patient in need thereof a composition including gaboxadol or a pharmaceutically acceptable salt thereof wherein the composition provides an in vivo plasma profile including a $C_{max}$ less than about 400 ng/ml and wherein the method provides improvement in the patient for more than 6 hours after administration of the gaboxadol or a pharmaceutically acceptable salt thereof. Methods of treating tics are described herein which include administering to a patient in need thereof gaboxadol or a pharmaceutically acceptable salt thereof wherein the method provides an in vivo plasma profile comprising a $AUC_{6-12}$ of less than about 900 ng·hr/ml and wherein the method provides improvement in the patient for more than 6 hours after administration of the gaboxadol or a pharmaceutically acceptable salt thereof. Methods of treating tics are described herein which include administering to a patient in need thereof a composition including gaboxadol or a pharmaceutically acceptable salt thereof wherein the composition provides an in vivo plasma profile comprising a $AUC_{6-12}$ of less than about 900 ng·hr/ml and wherein the method provides improvement in the patient for more than 6 hours after administration of the gaboxadol or a pharmaceutically acceptable salt thereof. Methods of treating tics are described herein which include administering to a patient in need thereof a first pharmaceutical composition including gaboxadol or a pharmaceutically acceptable salt thereof and a second pharmaceutical composition including gaboxadol or a pharmaceutically acceptable salt thereof wherein the second pharmaceutical composition provides an in vivo plasma profile having a mean $AUC_{0-\infty}$ of at least 20% less than the first pharmaceutical composition. Methods of treating tics are described herein which include administering to a patient in need thereof about 0.05 mg to about 30 mg gaboxadol or a pharmaceutically acceptable salt thereof in combination with a medicament selected from the group consisting of atypical neuroleptic agent and antihypertensive agent wherein the method provides improvement in the tics. Methods of treating tics are described herein which include administering to a patient in need thereof a composition including about 0.05 mg to about 30 mg gaboxadol or a pharmaceutically acceptable salt thereof in combination with a medicament selected from the group consisting of atypical neuroleptic agent and antihypertensive agent wherein the composition provides improvement in the tics.

Methods of treating stuttering include administering gaboxadol or a pharmaceutically acceptable salt thereof to a patient in need thereof to provide improvement in one or more stuttering symptoms. Pharmaceutical compositions including gaboxadol or a pharmaceutically acceptable salt thereof are provided for use in treating stuttering. Methods of treating stuttering include administering a pharmaceutical composition including gaboxadol or a pharmaceutically acceptable salt thereof to a patient in need thereof. In embodiments, methods of treating stuttering include administering gaboxadol or a pharmaceutically acceptable salt thereof to a patient in need thereof to provide improvement in stuttering symptoms in the patient a day after administration of the gaboxadol or a pharmaceutically acceptable salt thereof.

Methods of treating stuttering described herein include administering to a patient in need thereof about 0.05 mg to about 30 mg gaboxadol or a pharmaceutically acceptable salt thereof wherein the method provides improvement in the stuttering. Methods of treating stuttering described herein include administering to a patient in need thereof a composition including about 0.05 mg to about 30 mg gaboxadol or a pharmaceutically acceptable salt thereof wherein the composition provides improvement in the stuttering. Methods of treating stuttering described herein include administering to a patient in need thereof about 0.05 mg to about 30 mg gaboxadol or a pharmaceutically acceptable salt thereof wherein the method provides improvement in one or more stuttering symptoms. Methods of treating stuttering described herein include administering to a patient in need thereof a composition including about 0.05 mg to about 30 mg gaboxadol or a pharmaceutically acceptable salt thereof wherein the composition provides improvement in one or more stuttering symptoms. Methods of treating stuttering described herein include administering to a patient in need thereof about 0.05 mg to about 30 mg gaboxadol or a pharmaceutically acceptable salt thereof wherein the method provides improvement in the stuttering the next day. Methods of treating stuttering described herein include administering to a patient in need thereof a composition including about 0.05 mg to about 30 mg gaboxadol or a pharmaceutically acceptable salt thereof wherein the composition provides improvement in the stuttering the next day. Methods of treating stuttering described herein include administering to a patient in need thereof about 0.05 mg to about 30 mg gaboxadol or a pharmaceutically acceptable salt thereof wherein the method provides improvement in the patient for more than 6 hours after administration to the patient. Methods of treating stuttering described herein include administering to a patient in need thereof a composition including about 0.05 mg to about 30 mg gaboxadol or a pharmaceutically acceptable salt thereof wherein the composition provides improvement in the patient for more than 6 hours after administration to the patient. Methods of treating stuttering are described herein which include administering to a patient in need thereof gaboxadol or a pharmaceutically acceptable salt thereof wherein the method provides an in vivo plasma profile including a $C_{max}$ less than about 400 ng/ml and wherein the method provides improvement in the patient for more than 6 hours after administration of the gaboxadol or a pharmaceutically acceptable salt thereof. Methods of treating stuttering are described herein which include administering to a patient in need thereof a composition including gaboxadol or a pharmaceutically acceptable salt thereof wherein the composition provides an in vivo plasma profile including a $C_{max}$ less than about 400 ng/ml and wherein the method provides improvement in the patient for more than 6 hours after administration of the gaboxadol or a pharmaceutically acceptable salt thereof. Methods of treating stuttering are described herein which include administering to a patient in need thereof gaboxadol or a pharmaceutically acceptable salt thereof wherein the method provides an in vivo plasma profile comprising a $AUC_{6-12}$ of less than about 900 ng·hr/ml and wherein the method provides improvement in the patient for more than 6 hours after administration of the gaboxadol or a pharmaceutically acceptable salt thereof. Methods of treating stuttering are described herein which include administering to a patient in need thereof a composition including gaboxadol or a pharmaceutically acceptable salt thereof wherein the composition provides an in vivo plasma profile comprising a $AUC_{6-12}$ of less than about 900 ng·hr/ml and wherein the method provides improvement in the patient for more than 6 hours after administration of the gaboxadol or a pharmaceutically acceptable salt thereof. Methods of treating stuttering are described herein which include administering to a patient in need thereof a first pharmaceutical composition including gaboxadol or a pharmaceutically acceptable salt thereof and a second pharmaceutical composition including gaboxadol or a pharmaceutically acceptable salt thereof wherein the second pharmaceutical composition provides an in vivo plasma profile having a mean $AUC_{0-\infty}$ of at least 20% less than the first pharmaceutical composition. Methods of treating stuttering are described herein which include administering to a patient in need thereof about 0.05 mg to about 30 mg gaboxadol or a pharmaceutically acceptable salt thereof in combination with a medicament selected from the group consisting of atypical neuroleptic agent and antihypertensive agent wherein the method provides improvement in the stuttering. Methods of treating stuttering are described herein which include administering to a patient in need thereof a composition including about 0.05 mg to about 30 mg gaboxadol or a pharmaceutically acceptable salt thereof in combination with a medicament selected from the group consisting of atypical neuroleptic agent and antihypertensive agent wherein the composition provides improvement in the stuttering.

DETAILED DESCRIPTION

Figure 1:
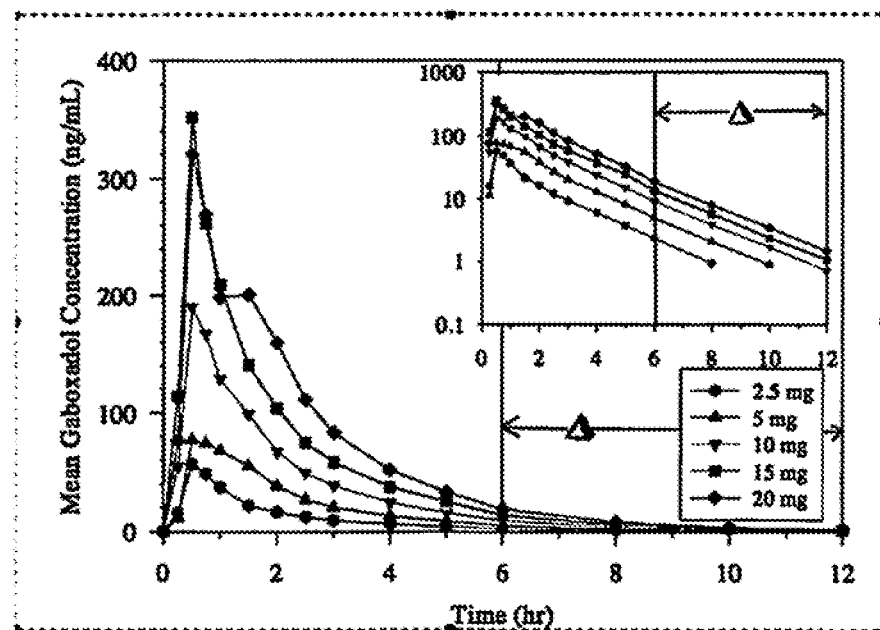
FIG. 1 shows the arithmetic mean plasma concentration-time profiles of gaboxadol following single oral doses (2.5, 5, 10, 15, and 20 mg) as described in Example 1 with horizontal lines A indicating the change between 6 and 12 hours.

Described herein are methods of treating Tourette syndrome (TS) with gaboxadol or a pharmaceutically acceptable salt thereof. Also described herein are methods of treating tics with gaboxadol or a pharmaceutically acceptable salt thereof. In embodiments, the tics are simple. In embodiments, the tics are complex. In embodiments, the tics are not associated with TS. Also described herein are methods of treating stuttering with gaboxadol or a pharmaceutically acceptable salt thereof. In embodiments, the stuttering is developmental. In embodiments, the stuttering is neurogenic.

Many pharmaceutical products are administered as a fixed dose, at regular intervals, to achieve therapeutic efficacy. Its duration of action is reflected by its plasma half-life. Gaboxadol is a selective $GABA_A$ receptor agonist with a relatively short half-life (t½=1.5 h). Since efficacy is often dependent on sufficient exposure within the central nervous system administration of CNS drugs with a short half-life may require frequent maintenance dosing.

Advantageously disclosed herein are methods of treating TS by administration of gaboxadol or a pharmaceutically acceptable salt thereof. For example, in embodiments, methods of treating TS are provided which include administering to a patient in need thereof a pharmaceutical composition including about 0.05 mg to about 30 mg gaboxadol or a pharmaceutically acceptable salt thereof wherein the composition provides improvement for more than 6 hours after administration to the patient.

Advantageously disclosed herein are methods of treating tics by administration of gaboxadol or a pharmaceutically acceptable salt thereof. For example, in embodiments, methods of treating tics are provided which include administering to a patient in need thereof a pharmaceutical composition including about 0.05 mg to about 30 mg gaboxadol or a pharmaceutically acceptable salt thereof wherein the composition provides improvement for more than 6 hours after administration to the patient.

Advantageously disclosed herein are methods of treating stuttering by administration of gaboxadol or a pharmaceutically acceptable salt thereof. For example, in embodiments, methods of treating stuttering are provided which include administering to a patient in need thereof a pharmaceutical composition including about 0.05 mg to about 30 mg gaboxadol or a pharmaceutically acceptable salt thereof wherein the composition provides improvement for more than 6 hours after administration to the patient.

Methods of treating TS described herein include administering to a patient in need thereof about 0.05 mg to about 30 mg gaboxadol or a pharmaceutically acceptable salt thereof wherein the method provides improvement in one or more symptoms of TS. Methods of treating TS described herein include administering to a patient in need thereof about 0.05 mg to about 30 mg gaboxadol or a pharmaceutically acceptable salt thereof wherein the method provides improvement in TS the next day. Methods of treating TS described herein include administering to a patient in need thereof about 0.05 mg to about 30 mg gaboxadol or a pharmaceutically acceptable salt thereof wherein the method provides improvement in the patient for more than 6 hours after administration to the patient. Methods of treating TS are described herein which include administering to a patient in need thereof gaboxadol or a pharmaceutically acceptable salt thereof wherein the method provides an in vivo plasma profile including a $C_{max}$ less than about 400 ng/ml and wherein the method provides improvement in the patient for more than 6 hours after administration of the gaboxadol or a pharmaceutically acceptable salt thereof. Methods of treating TS are described herein which include administering to a patient in need thereof gaboxadol or a pharmaceutically acceptable salt thereof wherein the method provides an in vivo plasma profile comprising a $AUC_{6-12}$ of less than about 900 ng ng·hr/ml and wherein the method provides improvement in the patient for more than 6 hours after administration of the gaboxadol or a pharmaceutically acceptable salt thereof. Methods of treating TS are described herein which include administering to a patient in need thereof a first pharmaceutical composition comprising gaboxadol or a pharmaceutically acceptable salt thereof and a second pharmaceutical composition comprising gaboxadol or a pharmaceutically acceptable salt thereof wherein the second pharmaceutical composition provides an in vivo plasma profile comprising a mean $AUC_{0-\infty}$ of at least 20% less than the first pharmaceutical composition.

Methods of treating tics described herein include administering to a patient in need thereof about 0.05 mg to about 30 mg gaboxadol or a pharmaceutically acceptable salt thereof wherein the method provides improvement in one or more symptoms of the tics. Methods of treating tics described herein include administering to a patient in need thereof about 0.05 mg to about 30 mg gaboxadol or a pharmaceutically acceptable salt thereof wherein the method provides improvement in the tics the next day. Methods of treating tics described herein include administering to a patient in need thereof about 0.05 mg to about 30 mg gaboxadol or a pharmaceutically acceptable salt thereof wherein the method provides improvement in the patient for more than 6 hours after administration to the patient. Methods of treating tics are described herein which include administering to a patient in need thereof gaboxadol or a pharmaceutically acceptable salt thereof wherein the method provides an in vivo plasma profile including a $C_{max}$ less than about 400 ng/ml and wherein the method provides improvement in the patient for more than 6 hours after administration of the gaboxadol or a pharmaceutically acceptable salt thereof. Methods of treating tics are described herein which include administering to a patient in need thereof gaboxadol or a pharmaceutically acceptable salt thereof wherein the method provides an in vivo plasma profile comprising a $AUC_{6-12}$ of less than about 900 ng ng·hr/ml and wherein the method provides improvement in the patient for more than 6 hours after administration of the gaboxadol or a pharmaceutically acceptable salt thereof. Methods of treating tics are described herein which include administering to a patient in need thereof a first pharmaceutical composition comprising gaboxadol or a pharmaceutically acceptable salt thereof and a second pharmaceutical composition comprising gaboxadol or a pharmaceutically acceptable salt thereof wherein the second pharmaceutical composition provides an in vivo plasma profile comprising a mean $AUC_{0-\infty}$ of at least 20% less than the first pharmaceutical composition.

Methods of treating stuttering described herein include administering to a patient in need thereof about 0.05 mg to about 30 mg gaboxadol or a pharmaceutically acceptable salt thereof wherein the method provides improvement in one or more symptoms of the stuttering. Methods of treating stuttering described herein include administering to a patient in need thereof about 0.05 mg to about 30 mg gaboxadol or a pharmaceutically acceptable salt thereof wherein the method provides improvement in the stuttering the next day. Methods of treating stuttering described herein include administering to a patient in need thereof about 0.05 mg to about 30 mg gaboxadol or a pharmaceutically acceptable salt thereof wherein the method provides improvement in the patient for more than 6 hours after administration to the patient. Methods of treating stuttering are described herein which include administering to a patient in need thereof gaboxadol or a pharmaceutically acceptable salt thereof wherein the method provides an in vivo plasma profile including a $C_{max}$ less than about 400 ng/ml and wherein the method provides improvement in the patient for more than 6 hours after administration of the gaboxadol or a pharmaceutically acceptable salt thereof. Methods of treating stuttering are described herein which include administering to a patient in need thereof gaboxadol or a pharmaceutically acceptable salt thereof wherein the method provides an in vivo plasma profile comprising a $AUC_{6-12}$ of less than about 900 ng ng·hr/ml and wherein the method provides improvement in the patient for more than 6 hours after administration of the gaboxadol or a pharmaceutically acceptable salt thereof. Methods of treating stuttering are described herein which include administering to a patient in need thereof a first pharmaceutical composition comprising gaboxadol or a pharmaceutically acceptable salt thereof and a second pharmaceutical composition comprising gaboxadol or a pharmaceutically acceptable salt thereof wherein the second pharmaceutical composition provides an in vivo plasma profile comprising a mean $AUC_{0-\infty}$ of at least 20% less than the first pharmaceutical composition.

Embodiments described herein provide that a patient in need thereof is administered a pharmaceutical composition including gaboxadol or a pharmaceutically acceptable salt thereof. Gaboxadol or pharmaceutically acceptable salt thereof may be provided as an acid addition salt, a zwitter ion hydrate, zwitter ion anhydrate, hydrochloride or hydrobromide salt, or in the form of the zwitter ion monohydrate. Acid addition salts, include but are not limited to, maleic, fumaric, benzoic, ascorbic, succinic, oxalic, bis-methylene-salicylic, methanesulfonic, ethane-disulfonic, acetic, propionic, tartaric, salicylic, citric, gluconic, lactic, malic, mandelic, cinnamic, citraconic, aspartic, stearic, palmitic, itaconic, glycolic, p-amino-benzoic, glutamic, benzene sulfonic or theophylline acetic acid addition salts, as well as the 8-halotheophyllines, for example 8-bromo-theophylline. In other suitable embodiments, inorganic acid addition salts, including but not limited to, hydrochloric, hydrobromic, sulfuric, sulfamic, phosphoric or nitric acid addition salts may be used.

In embodiments, gaboxadol is provided as gaboxadol monohydrate. One skilled in the art will readily understand that the amounts of active ingredient in a pharmaceutical composition will depend on the form of gaboxadol provided. For example, pharmaceutical compositions of including 5.0, 10.0, or 15.0 mg gaboxadol correspond to 5.6, 11.3, or 16.9 mg gaboxadol monohydrate.

In embodiments, gaboxadol is crystalline, such as the crystalline hydrochloric acid salt, the crystalline hydrobromic acid salt, or the crystalline zwitter ion monohydrate. In embodiments, gaboxadol is provided as a crystalline monohydrate.

Deuteration of pharmaceuticals to improve pharmacokinetics (PK), pharmacodynamics (PD), and toxicity profiles, has been demonstrated previously with some classes of drugs. Accordingly the use of deuterium enriched gaboxadol is contemplated and within the scope of the methods and compositions described herein. Deuterium can be incorporated in any position in replace of hydrogen synthetically, according to the synthetic procedures known in the art. For example, deuterium may be incorporated to various positions having an exchangeable proton, such as the amine N—H, via proton-deuterium equilibrium exchange. Thus, deuterium may be incorporated selectively or non-selectively through methods known in the art to provide deuterium enriched gaboxadol. See Journal of Labeled Compounds and Radiopharmaceuticals 19(5) 689-702 (1982).

Deuterium enriched gaboxadol may be described by the percentage of incorporation of deuterium at a given position in the molecule in the place of hydrogen. For example, deuterium enrichment of 1% at a given position means that 1% of molecules in a given sample contain deuterium at that specified position. The deuterium enrichment can be determined using conventional analytical methods, such as mass spectrometry and nuclear magnetic resonance spectroscopy. In embodiments deuterium enriched gaboxadol means that the specified position is enriched with deuterium above the naturally occurring distribution (i.e., above about 0156%). In embodiments deuterium enrichment is no less than about 1%, no less than about 5%, no less than about 10%, no less than about 20%, no less than about 50%, no less than about 70%, no less than about 80%, no less than about 90%, or no less than about 98% of deuterium at a specified position.

In embodiments, methods of treating TS include administering to a patient in need thereof a pharmaceutical composition including about 0.05 mg to about 30 mg gaboxadol or a pharmaceutically acceptable salt thereof. In embodiments, methods of treating tics include administering to a patient in need thereof a pharmaceutical composition including about 0.05 mg to about 30 mg gaboxadol or a pharmaceutically acceptable salt thereof. In embodiments, methods of treating stuttering include administering to a patient in need thereof a pharmaceutical composition including about 0.05 mg to about 30 mg gaboxadol or a pharmaceutically acceptable salt thereof In embodiments, the pharmaceutical compositions include 0.1 mg to 25 mg, 0.1 mg to 20 mg, 0.1 mg to 15 mg, 0.5 mg to 25 mg, 0.5 mg to 20 mg, 0.5 to 15 mg, 1 mg to 25 mg, 1 mg to 20 mg, 1 mg to 15 mg, 1.5 mg to 25 mg, 1.5 mg to 20 mg, 1.5 mg to 15 mg, 2 mg to 25 mg, 2 mg to 20 mg, 2 mg to 15 mg, 2.5 mg to 25 mg, 2.5 mg to 20 mg, 2.5 mg to 15 mg, 3 mg to 25 mg, 3 mg to 20 mg, 3 mg to 15 mg gaboxadol or a pharmaceutically acceptable salt thereof.

In embodiments, the pharmaceutical compositions include 5 mg to 20 mg, 5 mg to 10 mg, 4 mg to 6 mg, 6 mg to 8 mg, 8 mg to 10 mg, 10 mg to 12 mg, 12 mg to 14 mg, 14 mg to 16 mg, 16 mg to 18 mg, or 18 mg to 20 mg gaboxadol or a pharmaceutically acceptable salt thereof.

In embodiments, the pharmaceutical compositions include 0.1 mg, 0.25 mg, 0.5 mg, 1 mg, 2.5 mg, 3 mg, 4 mg, 5 mg, 7 mg, 7.5 mg, 8 mg, 8.5 mg, 9 mg, 9.5 mg, 10 mg, 10.5 mg, 11 mg, 12 mg, 12.5 mg, 13 mg, 14 mg, 15 mg, 16 mg, 17 mg, 17.5 mg, 18 mg, 19 mg, 20 mg, 21 mg, 22 mg, 23 mg, 24 mg, 25 mg, 26 mg, 27 mg, 28 mg, 29 mg, or 30 mg gaboxadol or a pharmaceutically acceptable salt thereof or amounts that are multiples of such doses. In embodiments, the pharmaceutical compositions include 2.5 mg, 5 mg, 7.5 mg, 10 mg, 15 mg, or 20 mg gaboxadol or a pharmaceutically acceptable salt thereof.

In embodiments, pharmaceutical compositions herein may be provided in the form of tablets, capsules, suppositories, inhalants, solutions, suspensions or emulsions. In embodiments, pharmaceutical compositions herein are suitable for parenteral administration, including, e.g., intramuscularly (i.m.), intravenously (i.v.), subcutaneously (s.c.), intraperitoneally (i.p.), or intrathecally (i.t.). The parenteral compositions herein must be sterile for administration by injection, infusion or implantation into the body and may be packaged in either single-dose or multi-dose containers. The parenteral compositions may be contained in a bag, a glass vial, a plastic vial, or a bottle.

In embodiments, liquid pharmaceutical compositions for parenteral administration to a subject including gaboxadol or a pharmaceutically acceptable salt thereof at a concentration of about 0.005 µg/ml to about 500 µg/ml are provided. In embodiments, the composition includes gaboxadol or a pharmaceutically acceptable salt thereof at a concentration of, e.g., about 0.005 µg/ml to about 250 µg/ml, about 0.005 µg/ml to about 200 µg/ml, about 0.005 µg/ml to about 150 µg/ml, about 0.005 µg/ml to about 100 µg/ml, or about 0.005 µg/ml to about 50 µg/ml.

In embodiments, compositions for parenteral administration include gaboxadol or a pharmaceutically acceptable salt thereof at a concentration of, e.g., about 0.05 µg/ml to about 50 µg/ml, about 0.1 µg/ml to about 50 µg/ml, about 0.05 µg/ml to about 25 µg/ml, about 0.05 µg/ml to about 10 µg/ml, about 0.05 µg/ml to about 5 µg/ml, or about 0.05 µg/ml to about 1 µg/ml. In embodiments, a composition for parenteral administration includes gaboxadol or a pharmaceutically acceptable salt thereof at a concentration of, e.g., about 0.05 µg/ml to about 15 µg/ml, about 0.5 µg/ml to about 10 µg/ml, about 0.5 µg/ml to about 7 µg/ml, about 1 µg/ml to about 10 µg/ml, about 5 µg/ml to about 10 µg/ml, or about 5 µg/ml to about 15 µg/ml. In embodiments, pharmaceutical compositions for parenteral administration are formulated as a total volume of about, e.g., 10 ml, 20 ml, 25 ml, 50 ml, 100 ml, 200 ml, 250 ml, or 500 ml.

In embodiments, compositions for parenteral administration including about 0.05 mg to about 100 mg gaboxadol or a pharmaceutically acceptable salt thereof are provided. In embodiments, the pharmaceutical compositions include about, e.g., 0.1 mg to 25 mg, 0.1 mg to 20 mg, 0.1 mg to 15 mg, 0.5 mg to 25 mg, 0.5 mg to 20 mg, 0.5 to 15 mg, 1 mg to 25 mg, 1 mg to 20 mg, 1 mg to 15 mg, 1.5 mg to 25 mg, 1.5 mg to 20 mg, 1.5 mg to 15 mg, 2 mg to 25 mg, 2 mg to 20 mg, 2 mg to 15 mg, 2.5 mg to 25 mg, 2.5 mg to 20 mg, 2.5 mg to 15 mg, 3 mg to 25 mg, 3 mg to 20 mg, 3 mg to 15 mg gaboxadol or a pharmaceutically acceptable salt thereof.

In embodiments, the pharmaceutical compositions for parenteral administration include about, e.g., 5 mg to 20 mg, 5 mg to 10 mg, 4 mg to 6 mg, 6 mg to 8 mg, 8 mg to 10 mg, 10 mg to 12 mg, 12 mg to 14 mg, 14 mg to 16 mg, 16 mg to 18 mg, or 18 mg to 20 mg gaboxadol or a pharmaceutically acceptable salt thereof. In embodiments, the pharmaceutical compositions for parenteral administration include about, e.g., 0.1 mg, 0.25 mg, 0.5 mg, 1 mg, 2.5 mg, 3 mg, 4 mg, 5 mg, 7 mg, 7.5 mg, 10 mg, 12.5 mg, 15 mg, 17.5 mg, 20 mg gaboxadol or a pharmaceutically acceptable salt thereof or amounts that are multiples of such doses.

In embodiments, pharmaceutical compositions for parenteral administration including gaboxadol or a pharmaceutically acceptable salt thereof wherein the gaboxadol or pharmaceutically acceptable salt thereof is present at a molarity less than about 1.0 M are provided. In embodiments, gaboxadol or pharmaceutically acceptable salt thereof is present at a molarity greater than, e.g., about 0.0001 M about 0.001 M, about 0.01 M, about 0.1 M, about 0.2 M, greater than about 0.5, greater than about 1.0 M, greater than about 1.2 M, greater than about 1.5 M, greater than about 1.75 M, greater than about 2.0 M, or greater than about 2.5 M. In embodiments, gaboxadol or pharmaceutically acceptable salt thereof is present at a molarity of between, e.g., about 0.00001 M to about 0.1 M, about 0.01 to about 0.1 M, about 0.1 M to about 1.0 M, about 1.0 M to about 5.0 M, or about 5.0 M to about 10.0 M. In embodiments, gaboxadol or pharmaceutically acceptable salt thereof is present at a molarity of less than, e.g., about 0.01 M, about 0.1 M, about 1.0 M, about 5.0 M, or about 10.0 M In embodiments, the solubility of gaboxadol or pharmaceutically acceptable salt thereof in the composition for parenteral administration is greater than, e.g., about 10 mg/mL, about 15 mg/mL, about 20 mg/mL, about 25 mg/mL, about 30 mg/mL, about 40 mg/mL, about 50 mg/mL, about 75 mg/mL, about 100 mg/mL, about 150 mg/mL, when measured, for example, in water at 25° C.

In embodiments, the solubility of gaboxadol or pharmaceutically acceptable salt thereof in the composition for parenteral administration is between, e.g., about 1 mg/mL to about 50 mg/mL, about 5 mg/mL to about 50 mg/mL, about 10 mg/mL to about 50 mg/mL, about 20 mg/mL to about 50 mg/ml, from about 20 mg/mL to about 30 mg/mL or from about 10 mg/mL to about 45 mg/mL, when measured, for example, in water at 25 C.

In embodiments, a pharmaceutical composition for parenteral administration is provided wherein the pharmaceutical composition is stable for at least six months. In embodiments, the pharmaceutical compositions herein exhibit no more than about 5% decrease in gaboxadol or pharmaceutically acceptable salt thereof after, e.g., 3 months or 6 months. In embodiments, the amount of gaboxadol or pharmaceutically acceptable salt thereof degradation is no more than about, e.g., 2.5%, 1%, 0.5% or 0.1%. In embodiments, the degradation of gaboxadol or pharmaceutically acceptable salt thereof is less than about, e.g., 5%, 2.5%, 1%, 0.5%, 0.25%, 0.1%, for at least six months.

In embodiments, pharmaceutical compositions for parenteral administration wherein the pharmaceutical composition remains soluble are provided. In embodiments, pharmaceutical compositions that are stable, soluble, local site compatible and/or ready-to-use are provided. In embodiments, the pharmaceutical compositions herein are ready-to-use for direct administration to a patient in need thereof.

The parenteral compositions herein may include one or more excipients, e.g., solvents, solubility enhancers, suspending agents, buffering agents, isotonicity agents, stabilizers or antimicrobial preservatives. When used, the excipients of the parenteral compositions will not adversely affect the stability, bioavailability, safety, and/or efficacy of gaboxadol or pharmaceutically acceptable salt used in the composition. Thus, parenteral compositions are provided wherein there is no incompatibility between any of the components of the dosage form.

Thus, in embodiments, parenteral compositions of gaboxadol or a pharmaceutically acceptable salt thereof including a stabilizing amount of at least one excipient are provided. For example, excipients may be selected buffering agents, solubilizing agents, tonicity agents, antioxidants, chelating agents, antimicrobial agents, preservatives, and combinations thereof. One skilled in the art will appreciate that an excipient may have more than one function and be classified in one or more defined group.

In embodiments, pharmaceutical compositions for parenteral administration are provided including gaboxadol, or a pharmaceutically acceptable salt thereof and an excipient wherein the excipient comprises a stabilizing amount of a buffering agent. In embodiments, the buffering agent can be a citrate, phosphate, acetate, tartrate, carbonate, glutamate, lactate, succinate, bicarbonate buffer and combinations thereof. For example, sodium citrate, trisodium citrate anhydrous, trisodium citrate dihydrate, sodium citrate dehydrate, triethanolamine (TRIS), trisodium citrate pentahydrate dihydrate (i.e., trisodium citrate dehydrate), acetic acid, citric acid, glutamic acid, phosphoric acid, may be used as a buffering agent. In embodiments, the buffering agent may be an amino acid, alkali metal, or alkaline earth metal buffer. For example, the buffering agent may be sodium acetate or hydrogen phosphate. In embodiments, provided herein are parenteral compositions of gaboxadol of pharmaceutically acceptable salts thereof wherein the pH of the composition is between about 4.0 to about 8.0. In embodiments, the pH of the compositions is between, e.g., about 5.0 to about 8.0, about 6.0 to about 8.0, about 6.5 to about 8.0. In embodiments, the pH of the compositions is between, e.g., about 6.5 to about 7.5, about 7.0 to about 7.8, about 7.2 to about 7.8, or about 7.3 to about 7.6. In embodiments, the pH of the aqueous solution of gaboxadol is, e.g., about 6.8, about 7.0, about 7.2, about 7.4, about 7.6, about 7.7, about 7.8, about 8.0, about 8.2, about 8.4, or about 8.6.

In embodiments, pharmaceutical compositions for parenteral administration are provided including gaboxadol, or a pharmaceutically acceptable salt thereof and an excipient wherein the excipient includes a solubilizing agent. For example, solubilizing agents according to the invention may include, e.g., sodium hydroxide, L-lysine, L-arginine, sodium carbonate, potassium carbonate, sodium phosphate, and/or potassium phosphate. In embodiments, provided herein are pharmaceutical compositions including gaboxadol, or a pharmaceutically acceptable salt thereof and an excipient wherein the excipient includes a particulate formation inhibitor. A particulate formation inhibitor refers to a compound that has the desired property of inhibiting the formation of particles in parenteral compositions. Particulate formation inhibitors of the invention include ethylenediaminetetraacetic acid (EDTA) and salts thereof, for example, ethylenediaminetetraacetic acid, calcium disodium salt (preferably as the hydrate); ethylenediaminetetraacetic acid, diammonium salt (preferably as the hydrate); ethylenediaminetetraacetic acid, dipotassium salt (preferably as the dihydrate); ethylenediaminetetraacetic acid, disodium salt (preferably as the dihydrate and, if desired, as the anhydrous form); ethylenediaminetetraacetic acid, tetrasodium salt (preferably as the hydrate); ethylenediaminetetraacetic acid, tripotassium salt (preferably as the dihydrate); ethylenediaminetetraacetic acid, trisodium salt (preferably as the hydrate) and ethylenediaminetetraacetic acid disodium salt, USP (preferably as the dihydrate).

In embodiments, provided herein are pharmaceutical compositions for parenteral administration including gaboxadol or a pharmaceutically acceptable salt thereof and an excipient wherein the excipient includes a solubilizing agent. For example, solubilizing agents may include, but are not limited to, acids, such as carboxylic acids, amino acids. In other examples, the solubilizing agents may be saturated carboxylic acids, unsaturated carboxylic acids, fatty acids, keto acids, aromatic carboxylic acids, dicarboxylic acids, tricarboxylic acids, α-hydroxy acids, amino acids, formic acid, acetic acid, propionic acid, butyric acid, valeric acid, caproic acid, enanthic acid, caprylic acid, pelargonic acid, capric acid, lauric acid, stearic acid, acrylic acid, docosahexaenoic acid, eicosapentaenoic acid, pyruvic acid, benzoic acid, salicylic acid, aldaric acid, oxalic acid, malonic acid, malic acid, succinic acid, glutaric acid, adipic acid, citric acid, lactic acid, alanine, arginine, aspargine, aspartic acid, cysteine, glutamine, glycine, histidine, isoleucine, leucine, lysine, methionine, phenylalanine, praline, serine, threonine, tryptophan, tyrosine, valine, and combinations thereof.

In embodiments, provided herein are pharmaceutical compositions for parenteral administration including gaboxadol or a pharmaceutically acceptable salt thereof and an excipient wherein the excipient renders the composition isotonic. Isotonic pharmaceutical compositions herein may be achieved by adding an appropriate quantity of sodium chloride, glucose, laevulose, dextrose, mannitol, or potassium chloride, or calcium chloride, or calcium gluconoglucoheptonate, or mixtures thereof. In embodiments, provided herein are pharmaceutical compositions including gaboxadol, or a pharmaceutically acceptable salt thereof and an excipient wherein the excipient includes a free radical antagonist. In embodiments, the free radical antagonist is ascorbic acid, ascorbic acid derivatives, organic compounds having at least one thiol, alkyl polyhydroxylated, and cycloalkyl polyhydroxylated compounds, and combinations thereof.

In embodiments, provided herein are pharmaceutical compositions for parenteral administration including gaboxadol, or a pharmaceutically acceptable salt thereof and an excipient wherein the excipient includes a preservative. In embodiments, the preservative is selected from benzalkonium chloride, benzethonium chloride, benzyl alcohol, chlorobutanol, chlorocresol, metacresol, Phenol, phenylmercuric nitrate, phenylmercuric acetate, methyl p-hydroxybenzoate, propyl p-hydroxybenzoate, butyl p-hydroxybenzoate, and thimerosal. In other embodiments, the preservative is selected from the group consisting of phenol, meta-cresol, benzyl alcohol, parabens (e.g., methyl, propyl, butyl), benzalkonium chloride, chlorobutanol, thimerosal, phenylmercuric salts (e.g., acetate, borate, or nitrate), and combinations thereof.

When administered, the parenteral compositions herein provide a time of maximum plasma concentration ($T_{max}$) for gaboxadol in human patients of about 1 or more hours (e.g., about 1.5 or more hours). In embodiments, a $T_{max}$ of gaboxadol in human patients ranging from between, e.g., about 1 to about 5 hours, about 1 to about 4 hours, about 1 to about 3 hours, about 1 to about 2 hours. In embodiments, a $T_{max}$ for gaboxadol in human patients of more than about 1.5 is observed. In embodiments, a $T_{max}$ for gaboxadol in human patients of less than about 3 hours is observed. The time of maximum plasma concentration is measured once infusion is complete.

In embodiments herein a dosage form includes from about 1 mg to about 500 mg gaboxadol, wherein parenteral administration (e.g., intramuscular, intravenous, subcutaneous, intraperitoneal, or intrathecal) of the dosage form provides an in vivo plasma profile for gaboxadol comprising a mean $AUC_{0-\infty}$ of more than about 25 ng·hr/ml. In embodiments, single dose administration of the dosage form provides an in vivo plasma profile for gaboxadol comprising a mean $AUC_{0-\infty}$ of more than about, e.g., 50 ng·hr/ml, 75 ng·hr/ml, 150 ng·hr/ml, 250 ng·hr/ml, 500 ng·hr/ml, 1000 ng·hr/ml, or 1500 ng·hr/ml.

In embodiments, the dosage form for parenteral administration includes from about 1 mg to about 500 mg gaboxadol, wherein administration of the dosage form provides an in vivo plasma profile for gaboxadol comprising a mean $C_{max}$ of less than about 10000 ng/ml. In embodiments, single dose administration of the compositions for parenteral administration provide an in vivo plasma profile for gaboxadol of a mean $C_{max}$ of less than about, e.g., 5000 ng/ml, 2500 ng/ml, 1000 ng/ml, 500 ng/ml, 250 ng/ml, or 100 ng/ml.

In embodiments, pharmaceutical compositions for parenteral administration include gaboxadol or a pharmaceutically acceptable salt thereof wherein parenteral administration exhibits a pharmacokinetic profile of a $T_{max}$ at about 1 to about 120 minutes after administration of the parenteral composition; followed by a plasma drug concentration of at least 50% $C_{max}$ for a duration of about 90 to about 360 minutes. In embodiments, parenteral administration of gaboxadol is followed by a plasma drug concentration of at least 50% $C_{max}$ for a duration of, e.g., about 10 to about 60 minutes, about 15 to about 90 minutes, about 30 to about 120 minutes, about 60 to about 180 minutes, about 90 to about 180 minutes.

Pharmaceutical compositions herein may be provided with immediate release, delayed release, extended release, or modified release profiles. In embodiments, pharmaceutical compositions with different drug release profiles may be combined to create a two phase or three-phase release profile. For example, pharmaceutical compositions may be provided with an immediate release and an extended release profile. In embodiments, pharmaceutical compositions may be provided with an extended release and delayed release profile. Such composition may be provided as pulsatile formulations, multilayer tablets, or capsules containing tablets, beads, granules, etc. Compositions may be prepared using a pharmaceutically acceptable "carrier" composed of materials that are considered safe and effective. The "carrier" includes all components present in the pharmaceutical formulation other than the active ingredient or ingredients. The term "carrier" includes, but is not limited to, diluents, binders, lubricants, disintegrants, fillers, and coating compositions.

In embodiments, the pharmaceutical compositions described herein may be administered once, twice, or three times daily, or every other day. In embodiments, a pharmaceutical composition described herein is provided to the patient in the evening. In embodiments, a pharmaceutical composition described herein is provided to the patient at bedtime. In embodiments, a pharmaceutical composition described herein is provided to the patient once in the evening and once in the morning. In embodiments, the total amount of gaboxadol or a pharmaceutically acceptable salt thereof administered to a subject in a 24-hour period is 1 mg to 30 mg. In embodiments, the total amount of gaboxadol or a pharmaceutically acceptable salt thereof administered to a subject in a 24-hour period is 1 mg to 20 mg. In embodiments, the total amount of gaboxadol or a pharmaceutically acceptable salt thereof administered to a subject in a 24-hour period is 5 mg, 10 mg, or 15 mg. In embodiments, the total amount of gaboxadol or a pharmaceutically acceptable salt thereof administered to a subject in a 24-hour period is 20 mg.

In embodiments, provided herein are methods of treating TS including administering to a patient in need thereof a pharmaceutical composition including gaboxadol or a pharmaceutically acceptable salt thereof wherein the composition provides improvement in at least one symptom of the TS. Symptoms of TS may include, but are not limited to, simple tics such as eye blinking and other eye movements, facial grimacing, shoulder shrugging, and head or shoulder jerking, simple vocalizations such as repetitive throat-clearing, sniffing, grunting and barking sounds. Complex symptoms of TS may include, but are not limited to, tics defined by distinct, coordinated patterns of movements involving several muscle groups, e.g., facial grimacing combined with a head twist and/or a shoulder shrug, sniffing or touching objects, hopping, jumping, bending, or twisting. More complex vocal tics can include words or phrases. Symptoms of TS can include more disabling tics, e.g., self harm tics such as punching oneself, or coprolalia (uttering swear words) or echolalia (repeating the words or phrases of others).

In embodiments, provided herein are methods of treating tics including administering to a patient in need thereof a pharmaceutical composition including gaboxadol or a pharmaceutically acceptable salt thereof wherein the composition provides improvement in at least one tic symptom. In embodiments, the tics are not associated with TS. Examples of various tics are described in the preceding paragraph.

In embodiments, provided herein are methods of treating stuttering including administering to a patient in need thereof a pharmaceutical composition including gaboxadol or a pharmaceutically acceptable salt thereof wherein the composition provides improvement in at least one stuttering symptom. Stuttering symptoms may include, but are not limited to, repetition of sounds, syllables, or words; prolongation of sounds; and interruptions in speech known as blocks. Stuttering symptoms may be accompanied by struggle behaviors, such as rapid eye blinks or tremors of the lips. Stuttering symptoms may be developmental or neurogenic.

In embodiments, provided herein are methods of treating TS including administering to a patient in need thereof a pharmaceutical composition including gaboxadol or a pharmaceutically acceptable salt thereof wherein the composition provides improvement of at least one TS symptom for more than 4 hours after administration of the pharmaceutical composition to the patient. In embodiments, the improvement of at least one TS symptom for more than 6 hours after administration of the pharmaceutical composition to the patient is provided in accordance with the present disclosure. In embodiments, improvement of at least one TS symptom for more than, e.g., 8 hours, 10 hours, 12 hours, 15 hours, 18 hours, 20 hours, or 24 hours after administration of the pharmaceutical composition to the patient is provided in accordance with the present disclosure. In embodiments, improvement in at least one TS symptom for at least e.g., 8 hours, 10 hours, 12 hours, 15 hours, 18 hours, 20 hours, or 24 hours after administration of the pharmaceutical composition to the patient is provided in accordance with the present disclosure. In embodiments, improvement in at least one TS symptom for 12 hours after administration of the pharmaceutical composition to the patient is provided in accordance with the present disclosure.

In embodiments, provided herein are methods of treating tics including administering to a patient in need thereof a pharmaceutical composition including gaboxadol or a pharmaceutically acceptable salt thereof wherein the composition provides improvement of at least one tics symptom for more than 4 hours after administration of the pharmaceutical composition to the patient. In embodiments, the improvement of at least one tics symptom for more than 6 hours after administration of the pharmaceutical composition to the patient is provided in accordance with the present disclosure. In embodiments, improvement of at least one tics symptom for more than, e.g., 8 hours, 10 hours, 12 hours, 15 hours, 18 hours, 20 hours, or 24 hours after administration of the pharmaceutical composition to the patient is provided in accordance with the present disclosure. In embodiments, improvement in at least one tics symptom for at least e.g., 8 hours, 10 hours, 12 hours, 15 hours, 18 hours, 20 hours, or 24 hours after administration of the pharmaceutical composition to the patient is provided in accordance with the present disclosure. In embodiments, improvement in at least one tics symptom for 12 hours after administration of the pharmaceutical composition to the patient is provided in accordance with the present disclosure.

In embodiments, provided herein are methods of treating stuttering including administering to a patient in need thereof a pharmaceutical composition including gaboxadol or a pharmaceutically acceptable salt thereof wherein the composition provides improvement of at least one stuttering symptom for more than 4 hours after administration of the pharmaceutical composition to the patient. In embodiments, the improvement of at least one stuttering symptom for more than 6 hours after administration of the pharmaceutical composition to the patient is provided in accordance with the present disclosure. In embodiments, improvement of at least one stuttering symptom for more than, e.g., 8 hours, 10 hours, 12 hours, 15 hours, 18 hours, 20 hours, or 24 hours after administration of the pharmaceutical composition to the patient is provided in accordance with the present disclosure. In embodiments, improvement in at least one stuttering symptom for at least e.g., 8 hours, 10 hours, 12 hours, 15 hours, 18 hours, 20 hours, or 24 hours after administration of the pharmaceutical composition to the patient is provided in accordance with the present disclosure. In embodiments, improvement in at least one symptom for 12 hours after administration of the pharmaceutical composition to the patient is provided in accordance with the present disclosure.

FIG. 1 shows the arithmetic mean plasma concentration-time profiles of gaboxadol following single oral doses (2.5, 5, 10, 15, and 20 mg)(see, Example 1, below) with horizontal lines A indicating the change between 6 and 12 hours. In embodiments, provided herein are methods of treating TS including administering to a patient in need thereof about 0.05 mg to about 30 mg gaboxadol or a pharmaceutically acceptable salt thereof which provides an in vivo plasma profile, wherein the in vivo plasma profile of the patient 6 hours after administration of the gaboxadol or pharmaceutically acceptable salt thereof is reduced by more than 50% and the method provides improvement in the patient for more than 6, 8, 10, 12, 14, 16, 18, 20, 22 or 24 hours after administration. In embodiments, provided herein are methods of treating TS including administering to a patient in need thereof about 0.05 mg to about 30 mg gaboxadol or a pharmaceutically acceptable salt thereof which provides an in vivo plasma profile, wherein the in vivo plasma profile of the patient 6 hours after administration of the gaboxadol or pharmaceutically acceptable salt thereof is reduced by more than 55% and the method provides improvement in the patient for more than 6, 8, 10, 12, 14, 16, 18, 20, 22 or 24 hours after administration. In embodiments, provided herein are methods of treating TS including administering to a patient in need thereof about 0.05 mg to about 30 mg gaboxadol or a pharmaceutically acceptable salt thereof which provides an in vivo plasma profile, wherein the in vivo plasma profile of the patient 6 hours after administration of the gaboxadol or pharmaceutically acceptable salt thereof is reduced by more than 60% and the method provides improvement in the patient for more than 6, 8, 10, 12, 14, 16, 18, 20, 22 or 24 hours after administration. In embodiments, provided herein are methods of treating TS including administering to a patient in need thereof about 0.05 mg to about 30 mg gaboxadol or a pharmaceutically acceptable salt thereof which provides an in vivo plasma profile, wherein the in vivo plasma profile of the patient 6 hours after administration of the gaboxadol or pharmaceutically acceptable salt thereof is reduced by more than 65% and the method provides improvement in the patient for more than 6, 8, 10, 12, 14, 16, 18, 20, 22 or 24 hours after administration. In embodiments, provided herein are methods of treating TS including administering to a patient in need thereof about 0.05 mg to about 30 mg gaboxadol or a pharmaceutically acceptable salt thereof which provides an in vivo plasma profile, wherein the in vivo plasma profile of the patient 6 hours after administration of the gaboxadol or pharmaceutically acceptable salt thereof is reduced by more than 70% and the method provides improvement in the patient for more than 6, 8, 10, 12, 14, 16, 18, 20, 22 or 24 hours after administration. In embodiments, provided herein are methods of treating TS including administering to a patient in need thereof about 0.05 mg to about 30 mg gaboxadol or a pharmaceutically acceptable salt thereof which provides an in vivo plasma profile, wherein the in vivo plasma profile of the patient 6 hours after administration of the gaboxadol or pharmaceutically acceptable salt thereof is reduced by more than 75% and the method provides improvement in the patient for more than 6, 8, 10, 12, 14, 16, 18, 20, 22 or 24 hours after administration.

In embodiments, provided herein are methods of treating TS wherein the amount of gaboxadol or pharmaceutically acceptable salt thereof within the patient about 4 hours after administration of the pharmaceutical composition is less than about 75% of the administered dose. In embodiments, provided herein are methods wherein the amount of gaboxadol or pharmaceutically acceptable salt thereof within the patient about, e.g., 6 hours, 8 hours, 10 hours, 12 hours, 15 hours, or 20 hours after administration of the pharmaceutical composition is less than about 75%.

In embodiments, provided herein are methods of treating TS wherein the amount of gaboxadol or pharmaceutically acceptable salt thereof within the patient about 4 hours after administration of the pharmaceutical composition is less than about 80% of the administered dose. In embodiments, provided herein are methods wherein the amount of gaboxadol or pharmaceutically acceptable salt thereof within the patient about, e.g., 6 hours, 8 hours, 10 hours, 12 hours, 15 hours, or 20 hours after administration of the pharmaceutical composition is less than about 80% of the administered dose.

In embodiments, provided herein are methods of treating TS wherein the amount of gaboxadol or pharmaceutically acceptable salt thereof within the patient about 4 hours after administration of the pharmaceutical composition is between about 65% to about 85% of the administered dose. In embodiments, the amount of gaboxadol or pharmaceutically acceptable salt thereof within the patient after about, e.g., 6 hours, 8 hours, 10 hours, 12 hours, 15 hours, or 20 hours after administration of the pharmaceutical composition is between about 65% to about 85% of the administered dose.

In embodiments, provided herein are methods of treating TS including administering to a patient in need thereof a pharmaceutical composition including gaboxadol or a pharmaceutically acceptable salt thereof wherein the composition provides an in vivo plasma concentration 6 hours after administration which is less than 75% of the administered dose and provides improvement in the patient for more than 6, 8, 10, 12, 14, 16, 18, 20, 22 or 24 hours after administration. In embodiments, provided herein are methods of treating TS including administering to a patient in need thereof a pharmaceutical composition including gaboxadol or a pharmaceutically acceptable salt thereof wherein the composition provides an in vivo plasma concentration 6 hours after administration which is less than 80% of the administered dose and provides improvement in the patient for more than 6, 8, 10, 12, 14, 16, 18, 20, 22 or 24 hours after administration. In embodiments, provided herein are methods of treating TS including administering to a patient in need thereof a pharmaceutical composition including gaboxadol or a pharmaceutically acceptable salt thereof wherein the composition provides an in vivo plasma concentration 6 hours after administration which is less than 85% of the administered dose and provides improvement in the patient for more than 6, 8, 10, 12, 14, 16, 18, 20, 22 or 24 hours after administration. In embodiments, provided herein are methods of treating TS including administering to a patient in need thereof a pharmaceutical composition including gaboxadol or a pharmaceutically acceptable salt thereof wherein the composition provides an in vivo plasma concentration 6 hours after administration which is less than 90% of the administered dose and provides improvement in the patient for more than 6, 8, 10, 12, 14, 16, 18, 20, 22 or 24 hours after administration. In embodiments, provided herein are methods of treating TS including administering to a patient in need thereof a pharmaceutical composition including gaboxadol or a pharmaceutically acceptable salt thereof wherein the composition provides an in vivo plasma concentration 6 hours after administration which is less than 95% of the administered dose and provides improvement in the patient for more than 6, 8, 10, 12, 14, 16, 18, 20, 22 or 24 hours after administration. In embodiments, provided herein are methods of treating TS including administering to a patient in need thereof a pharmaceutical composition including gaboxadol or a pharmaceutically acceptable salt thereof wherein the composition provides an in vivo plasma concentration 6 hours after administration which is less than 100% of the administered dose and provides improvement in the patient for more than 6, 8, 10, 12, 14, 16, 18, 20, 22 or 24 hours after administration.

In embodiments, provided herein are methods of treating tics including administering to a patient in need thereof about 0.05 mg to about 30 mg gaboxadol or a pharmaceutically acceptable salt thereof which provides an in vivo plasma profile, wherein the in vivo plasma profile of the patient 6 hours after administration of the gaboxadol or pharmaceutically acceptable salt thereof is reduced by more than 50% and the method provides improvement in the patient for more than 6, 8, 10, 12, 14, 16, 18, 20, 22 or 24 hours after administration. In embodiments, provided herein are methods of treating tics including administering to a patient in need thereof about 0.05 mg to about 30 mg gaboxadol or a pharmaceutically acceptable salt thereof which provides an in vivo plasma profile, wherein the in vivo plasma profile of the patient 6 hours after administration of the gaboxadol or pharmaceutically acceptable salt thereof is reduced by more than 55% and the method provides improvement in the patient for more than 6, 8, 10, 12, 14, 16, 18, 20, 22 or 24 hours after administration. In embodiments, provided herein are methods of treating tics including administering to a patient in need thereof about 0.05 mg to about 30 mg gaboxadol or a pharmaceutically acceptable salt thereof which provides an in vivo plasma profile, wherein the in vivo plasma profile of the patient 6 hours after administration of the gaboxadol or pharmaceutically acceptable salt thereof is reduced by more than 60% and the method provides improvement in the patient for more than 6, 8, 10, 12, 14, 16, 18, 20, 22 or 24 hours after administration. In embodiments, provided herein are methods of treating tics including administering to a patient in need thereof about 0.05 mg to about 30 mg gaboxadol or a pharmaceutically acceptable salt thereof which provides an in vivo plasma profile, wherein the in vivo plasma profile of the patient 6 hours after administration of the gaboxadol or pharmaceutically acceptable salt thereof is reduced by more than 65% and the method provides improvement in the patient for more than 6, 8, 10, 12, 14, 16, 18, 20, 22 or 24 hours after administration. In embodiments, provided herein are methods of treating tics including administering to a patient in need thereof about 0.05 mg to about 30 mg gaboxadol or a pharmaceutically acceptable salt thereof which provides an in vivo plasma profile, wherein the in vivo plasma profile of the patient 6 hours after administration of the gaboxadol or pharmaceutically acceptable salt thereof is reduced by more than 70% and the method provides improvement in the patient for more than 6, 8, 10, 12, 14, 16, 18, 20, 22 or 24 hours after administration. In embodiments, provided herein are methods of treating tics including administering to a patient in need thereof about 0.05 mg to about 30 mg gaboxadol or a pharmaceutically acceptable salt thereof which provides an in vivo plasma profile, wherein the in vivo plasma profile of the patient 6 hours after administration of the gaboxadol or pharmaceutically acceptable salt thereof is reduced by more than 75% and the method provides improvement in the patient for more than 6, 8, 10, 12, 14, 16, 18, 20, 22 or 24 hours after administration.

In embodiments, provided herein are methods of treating tics wherein the amount of gaboxadol or pharmaceutically acceptable salt thereof within the patient about 4 hours after administration of the pharmaceutical composition is less than about 75% of the administered dose. In embodiments, provided herein are methods wherein the amount of gaboxadol or pharmaceutically acceptable salt thereof within the patient about, e.g., 6 hours, 8 hours, 10 hours, 12 hours, 15 hours, or 20 hours after administration of the pharmaceutical composition is less than about 75%.

In embodiments, provided herein are methods of treating tics wherein the amount of gaboxadol or pharmaceutically acceptable salt thereof within the patient about 4 hours after administration of the pharmaceutical composition is less than about 80% of the administered dose. In embodiments, provided herein are methods wherein the amount of gaboxadol or pharmaceutically acceptable salt thereof within the patient about, e.g., 6 hours, 8 hours, 10 hours, 12 hours, 15 hours, or 20 hours after administration of the pharmaceutical composition is less than about 80% of the administered dose.

In embodiments, provided herein are methods of treating tics wherein the amount of gaboxadol or pharmaceutically acceptable salt thereof within the patient about 4 hours after administration of the pharmaceutical composition is between about 65% to about 85% of the administered dose. In embodiments, the amount of gaboxadol or pharmaceutically acceptable salt thereof within the patient after about, e.g., 6 hours, 8 hours, 10 hours, 12 hours, 15 hours, or 20 hours after administration of the pharmaceutical composition is between about 65% to about 85% of the administered dose.

In embodiments, provided herein are methods of treating tics including administering to a patient in need thereof a pharmaceutical composition including gaboxadol or a pharmaceutically acceptable salt thereof wherein the composition provides an in vivo plasma concentration 6 hours after administration which is less than 75% of the administered dose and provides improvement in the patient for more than 6, 8, 10, 12, 14, 16, 18, 20, 22 or 24 hours after administration. In embodiments, provided herein are methods of treating tics including administering to a patient in need thereof a pharmaceutical composition including gaboxadol or a pharmaceutically acceptable salt thereof wherein the composition provides an in vivo plasma concentration 6 hours after administration which is less than 80% of the administered dose and provides improvement in the patient for more than 6, 8, 10, 12, 14, 16, 18, 20, 22 or 24 hours after administration. In embodiments, provided herein are methods of treating tics including administering to a patient in need thereof a pharmaceutical composition including gaboxadol or a pharmaceutically acceptable salt thereof wherein the composition provides an in vivo plasma concentration 6 hours after administration which is less than 85% of the administered dose and provides improvement in the patient for more than 6, 8, 10, 12, 14, 16, 18, 20, 22 or 24 hours after administration. In embodiments, provided herein are methods of treating tics including administering to a patient in need thereof a pharmaceutical composition including gaboxadol or a pharmaceutically acceptable salt thereof wherein the composition provides an in vivo plasma concentration 6 hours after administration which is less than 90% of the administered dose and provides improvement in the patient for more than 6, 8, 10, 12, 14, 16, 18, 20, 22 or 24 hours after administration. In embodiments, provided herein are methods of treating tics including administering to a patient in need thereof a pharmaceutical composition including gaboxadol or a pharmaceutically acceptable salt thereof wherein the composition provides an in vivo plasma concentration 6 hours after administration which is less than 95% of the administered dose and provides improvement in the patient for more than 6, 8, 10, 12, 14, 16, 18, 20, 22 or 24 hours after administration. In embodiments, provided herein are methods of treating tics including administering to a patient in need thereof a pharmaceutical composition including gaboxadol or a pharmaceutically acceptable salt thereof wherein the composition provides an in vivo plasma concentration 6 hours after administration which is less than 100% of the administered dose and provides improvement in the patient for more than 6, 8, 10, 12, 14, 16, 18, 20, 22 or 24 hours after administration.

In embodiments, provided herein are methods of treating stuttering including administering to a patient in need thereof about 0.05 mg to about 30 mg gaboxadol or a pharmaceutically acceptable salt thereof which provides an in vivo plasma profile, wherein the in vivo plasma profile of the patient 6 hours after administration of the gaboxadol or pharmaceutically acceptable salt thereof is reduced by more than 50% and the method provides improvement in the patient for more than 6, 8, 10, 12, 14, 16, 18, 20, 22 or 24 hours after administration. In embodiments, provided herein are methods of treating stuttering including administering to a patient in need thereof about 0.05 mg to about 30 mg gaboxadol or a pharmaceutically acceptable salt thereof which provides an in vivo plasma profile, wherein the in vivo plasma profile of the patient 6 hours after administration of the gaboxadol or pharmaceutically acceptable salt thereof is reduced by more than 55% and the method provides improvement in the patient for more than 6, 8, 10, 12, 14, 16, 18, 20, 22 or 24 hours after administration. In embodiments, provided herein are methods of treating stuttering including administering to a patient in need thereof about 0.05 mg to about 30 mg gaboxadol or a pharmaceutically acceptable salt thereof which provides an in vivo plasma profile, wherein the in vivo plasma profile of the patient 6 hours after administration of the gaboxadol or pharmaceutically acceptable salt thereof is reduced by more than 60% and the method provides improvement in the patient for more than 6, 8, 10, 12, 14, 16, 18, 20, 22 or 24 hours after administration. In embodiments, provided herein are methods of treating stuttering including administering to a patient in need thereof about 0.05 mg to about 30 mg gaboxadol or a pharmaceutically acceptable salt thereof which provides an in vivo plasma profile, wherein the in vivo plasma profile of the patient 6 hours after administration of the gaboxadol or pharmaceutically acceptable salt thereof is reduced by more than 65% and the method provides improvement in the patient for more than 6, 8, 10, 12, 14, 16, 18, 20, 22 or 24 hours after administration. In embodiments, provided herein are methods of treating stuttering including administering to a patient in need thereof about 0.05 mg to about 30 mg gaboxadol or a pharmaceutically acceptable salt thereof which provides an in vivo plasma profile, wherein the in vivo plasma profile of the patient 6 hours after administration of the gaboxadol or pharmaceutically acceptable salt thereof is reduced by more than 70% and the method provides improvement in the patient for more than 6, 8, 10, 12, 14, 16, 18, 20, 22 or 24 hours after administration. In embodiments, provided herein are methods of treating stuttering including administering to a patient in need thereof about 0.05 mg to about 30 mg gaboxadol or a pharmaceutically acceptable salt thereof which provides an in vivo plasma profile, wherein the in vivo plasma profile of the patient 6 hours after administration of the gaboxadol or pharmaceutically acceptable salt thereof is reduced by more than 75% and the method provides improvement in the patient for more than 6, 8, 10, 12, 14, 16, 18, 20, 22 or 24 hours after administration.

In embodiments, provided herein are methods of treating stuttering wherein the amount of gaboxadol or pharmaceutically acceptable salt thereof within the patient about 4 hours after administration of the pharmaceutical composition is less than about 75% of the administered dose. In embodiments, provided herein are methods wherein the amount of gaboxadol or pharmaceutically acceptable salt thereof within the patient about, e.g., 6 hours, 8 hours, 10 hours, 12 hours, 15 hours, or 20 hours after administration of the pharmaceutical composition is less than about 75%.

In embodiments, provided herein are methods of treating stuttering wherein the amount of gaboxadol or pharmaceutically acceptable salt thereof within the patient about 4 hours after administration of the pharmaceutical composition is less than about 80% of the administered dose. In embodiments, provided herein are methods wherein the amount of gaboxadol or pharmaceutically acceptable salt thereof within the patient about, e.g., 6 hours, 8 hours, 10 hours, 12 hours, 15 hours, or 20 hours after administration of the pharmaceutical composition is less than about 80% of the administered dose.

In embodiments, provided herein are methods of treating stuttering wherein the amount of gaboxadol or pharmaceutically acceptable salt thereof within the patient about 4 hours after administration of the pharmaceutical composition is between about 65% to about 85% of the administered dose. In embodiments, the amount of gaboxadol or pharmaceutically acceptable salt thereof within the patient after about, e.g., 6 hours, 8 hours, 10 hours, 12 hours, 15 hours, or 20 hours after administration of the pharmaceutical composition is between about 65% to about 85% of the administered dose.

In embodiments, provided herein are methods of treating stuttering including administering to a patient in need thereof a pharmaceutical composition including gaboxadol or a pharmaceutically acceptable salt thereof wherein the composition provides an in vivo plasma concentration 6 hours after administration which is less than 75% of the administered dose and provides improvement in the patient for more than 6, 8, 10, 12, 14, 16, 18, 20, 22 or 24 hours after administration. In embodiments, provided herein are methods of treating stuttering including administering to a patient in need thereof a pharmaceutical composition including gaboxadol or a pharmaceutically acceptable salt thereof wherein the composition provides an in vivo plasma concentration 6 hours after administration which is less than 80% of the administered dose and provides improvement in the patient for more than 6, 8, 10, 12, 14, 16, 18, 20, 22 or 24 hours after administration. In embodiments, provided herein are methods of treating stuttering including administering to a patient in need thereof a pharmaceutical composition including gaboxadol or a pharmaceutically acceptable salt thereof wherein the composition provides an in vivo plasma concentration 6 hours after administration which is less than 85% of the administered dose and provides improvement in the patient for more than 6, 8, 10, 12, 14, 16, 18, 20, 22 or 24 hours after administration. In embodiments, provided herein are methods of treating stuttering including administering to a patient in need thereof a pharmaceutical composition including gaboxadol or a pharmaceutically acceptable salt thereof wherein the composition provides an in vivo plasma concentration 6 hours after administration which is less than 90% of the administered dose and provides improvement in the patient for more than 6, 8, 10, 12, 14, 16, 18, 20, 22 or 24 hours after administration. In embodiments, provided herein are methods of treating stuttering including administering to a patient in need thereof a pharmaceutical composition including gaboxadol or a pharmaceutically acceptable salt thereof wherein the composition provides an in vivo plasma concentration 6 hours after administration which is less than 95% of the administered dose and provides improvement in the patient for more than 6, 8, 10, 12, 14, 16, 18, 20, 22 or 24 hours after administration. In embodiments, provided herein are methods of treating stuttering including administering to a patient in need thereof a pharmaceutical composition including gaboxadol or a pharmaceutically acceptable salt thereof wherein the composition provides an in vivo plasma concentration 6 hours after administration which is less than 100% of the administered dose and provides improvement in the patient for more than 6, 8, 10, 12, 14, 16, 18, 20, 22 or 24 hours after administration.

In embodiments, provided herein are methods of treating TS including administering to a patient in need thereof a pharmaceutical composition including gaboxadol or a pharmaceutically acceptable salt thereof wherein the composition provides an in vivo plasma profile having a $C_{max}$ less than about 500 ng/ml. In embodiments, the composition provides improvement for more than 6 hours after administration to the patient.

In embodiments, the composition provides an in vivo plasma profile having a $C_{max}$ less than about, e.g., 450 ng/ml, 400 ng/ml 350 ng/ml, or 300 ng/ml and wherein the composition provides improvement in one or more symptoms of TS a day after administration. In embodiments, the composition provides an in vivo plasma profile having a $C_{max}$ less than about, e.g., 250 ng/ml, 200 ng/ml 150 ng/ml, or 100 ng/ml and wherein the composition provides improvement in one or more symptoms of TS a day after administration.

In embodiments, provided herein are methods of treating TS including administering to a patient in need thereof a pharmaceutical composition including gaboxadol or a pharmaceutically acceptable salt thereof wherein the composition provides an in vivo plasma profile having a $AUC_{0-\infty}$ of less than about 900 ng·hr/ml. In embodiments, the composition provides improvement in one or more symptoms of TS a day after administration. In embodiments, the compositions provide an in vivo plasma profile having a $AUC_{0-\infty}$ of less than about, e.g., 850 ng·hr/ml, 800 ng·hr/ml, 750 ng·hr/ml, or 700 ng·hr/ml and wherein the composition provides improvement in one or more symptoms of TS a day after administration. In embodiments, the composition provides improvement in one or more TS symptoms for more than 6 hours after administration.

In embodiments, provided herein are methods of treating TS including administering to a patient in need thereof a pharmaceutical composition including gaboxadol or a pharmaceutically acceptable salt thereof wherein the composition provides an in vivo plasma profile having a $AUC_{0-\infty}$ of less than about, e.g., 650 ng·hr/ml, 600 ng·hr/ml, 550 ng·hr/ml, 500 ng·hr/ml, or 450 ng·hr/ml. In embodiments, wherein the composition provides an in vivo plasma profile having a $AUC_{0-\infty}$ of less than about, e.g., 400 ng·hr/ml, 350 ng·hr/ml, 300 ng·hr/ml, 250 ng·hr/ml, or 200 ng·hr/ml. In embodiments, the composition provides an in vivo plasma profile having a $AUC_{0-\infty}$ of less than about, e.g., 150 ng·hr/ml, 100 ng·hr/ml, 75 ng·hr/ml, or 50 ng·hr/ml. In embodiments, the composition provides improvement symptoms of TS for more than, e.g., 4 hours, 6 hours, 8 hours, 10 hours, or 12 hours, after administration of the composition to the patient.

In embodiments, provided herein are methods of treating TS including administering to a patient in need thereof an amount of gaboxadol or a pharmaceutically acceptable salt thereof which provides an in vivo plasma profile having a $AUC_{6-12}$ which is less than 75% of the $C_{max}$ and provides improvement in the patient for more than 6, 8, 10, 12, 14, 16, 18, 20, 22 or 24 hours after administration. In embodiments, provided herein are methods of treating TS including administering to a patient in need thereof an amount of gaboxadol or a pharmaceutically acceptable salt thereof which provides an in vivo plasma profile having a $AUC_{6-12}$ which is less than 80% of the $C_{max}$ and provides improvement in the patient for more than 6, 8, 10, 12, 14, 16, 18, 20, 22 or 24 hours after administration. In embodiments, provided herein are methods of treating TS including administering to a patient in need thereof an amount of gaboxadol or a pharmaceutically acceptable salt thereof which provides an in vivo plasma profile having a $AUC_{6-12}$ which is less than 85% of the $C_{max}$ and provides improvement in the patient for more than 6, 8, 10, 12, 14, 16, 18, 20, 22 or 24 hours after administration. In embodiments, provided herein are methods of treating TS including administering to a patient in need thereof an amount of gaboxadol or a pharmaceutically acceptable salt thereof which provides an in vivo plasma profile having a $AUC_{6-12}$ which is less than 90% of the $C_{max}$ and provides improvement in the patient for more than 6, 8, 10, 12, 14, 16, 18, 20, 22 or 24 hours after administration. In embodiments, provided herein are methods of treating TS including administering to a patient in need thereof an amount of gaboxadol or a pharmaceutically acceptable salt thereof which provides an in vivo plasma profile having a $AUC_{6-12}$ which is less than 95% of the $C_{max}$ and provides improvement in the patient for more than 6, 8, 10, 12, 14, 16, 18, 20, 22 or 24 hours after administration. In embodiments, provided herein are methods of treating TS including administering to a patient in need thereof an amount of gaboxadol or a pharmaceutically acceptable salt thereof which provides an in vivo plasma profile having a $AUC_{6-12}$ which is less than 100% of the $C_{max}$ and provides improvement in the patient for more than 6, 8, 10, 12, 14, 16, 18, 20, 22 or 24 hours after administration.

In embodiments, provided herein are methods of treating TS including administering to a patient in need thereof a pharmaceutical composition including gaboxadol or a pharmaceutically acceptable salt thereof wherein the composition provides an in vivo plasma profile having a $AUC_{6-12}$ which is less than 75% of the $C_{max}$ and provides improvement in the patient for more than 6, 8, 10, 12, 14, 16, 18, 20, 22 or 24 hours after administration. In embodiments, provided herein are methods of treating TS including administering to a patient in need thereof a pharmaceutical composition including gaboxadol or a pharmaceutically acceptable salt thereof wherein the composition provides an in vivo plasma profile having a $AUC_{6-12}$ which is less than 80% of the $C_{max}$ and provides improvement in the patient for more than 6, 8, 10, 12, 14, 16, 18, 20, 22 or 24 hours after administration. In embodiments, provided herein are methods of treating TS including administering to a patient in need thereof a pharmaceutical composition including gaboxadol or a pharmaceutically acceptable salt thereof wherein the composition provides an in vivo plasma profile having a $AUC_{6-12}$ which is less than 85% of the $C_{max}$ and provides improvement in the patient for more than 6, 8, 10, 12, 14, 16, 18, 20, 22 or 24 hours after administration. In embodiments, provided herein are methods of treating TS including administering to a patient in need thereof a pharmaceutical composition including gaboxadol or a pharmaceutically acceptable salt thereof wherein the composition provides an in vivo plasma profile having a $AUC_{6-12}$ which is less than 90% of the $C_{max}$ and provides improvement in the patient for more than 6, 8, 10, 12, 14, 16, 18, 20, 22 or 24 hours after administration. In embodiments, provided herein are methods of treating TS including administering to a patient in need thereof a pharmaceutical composition including gaboxadol or a pharmaceutically acceptable salt thereof wherein the composition provides an in vivo plasma profile having a $AUC_{6-12}$ which is less than 95% of the $C_{max}$ and provides improvement in the patient for more than 6, 8, 10, 12, 14, 16, 18, 20, 22 or 24 hours after administration. In embodiments, provided herein are methods of treating TS including administering to a patient in need thereof a pharmaceutical composition including gaboxadol or a pharmaceutically acceptable salt thereof wherein the composition provides an in vivo plasma profile having a $AUC_{6-12}$ which is less than 100% of the $C_{max}$ and provides improvement in the patient for more than 6, 8, 10, 12, 14, 16, 18, 20, 22 or 24 hours after administration.

In embodiments, provided herein are methods of treating TS including administering to a patient in need thereof a pharmaceutical composition including gaboxadol or a pharmaceutically acceptable salt thereof wherein the composition provides an in vivo plasma profile having a $AUC_{6-12}$ which is less than 75% of the administered dose and provides improvement in the patient for more than 6, 8, 10, 12, 14, 16, 18, 20, 22 or 24 hours after administration. In embodiments, provided herein are methods of treating TS including administering to a patient in need thereof a pharmaceutical composition including gaboxadol or a pharmaceutically acceptable salt thereof wherein the composition provides an in vivo plasma profile having a $AUC_{6-12}$ which is less than 80% of the administered dose and provides improvement in the patient for more than 6, 8, 10, 12, 14, 16, 18, 20, 22 or 24 hours after administration. In embodiments, provided herein are methods of treating TS including administering to a patient in need thereof a pharmaceutical composition including gaboxadol or a pharmaceutically acceptable salt thereof wherein the composition provides an in vivo plasma profile having a $AUC_{6-12}$ which is less than 85% of the administered dose and provides improvement in the patient for more than 6, 8, 10, 12, 14, 16, 18, 20, 22 or 24 hours after administration. In embodiments, provided herein are methods of treating TS including administering to a patient in need thereof a pharmaceutical composition including gaboxadol or a pharmaceutically acceptable salt thereof wherein the composition provides an in vivo plasma profile having a $AUC_{6-12}$ which is less than 90% of the administered dose and provides improvement in the patient for more than 6, 8, 10, 12, 14, 16, 18, 20, 22 or 24 hours after administration. In embodiments, provided herein are methods of treating TS including administering to a patient in need thereof a pharmaceutical composition including gaboxadol or a pharmaceutically acceptable salt thereof wherein the composition provides an in vivo plasma profile having a $AUC_{6-12}$ which is less than 95% of the administered dose and provides improvement in the patient for more than 6, 8, 10, 12, 14, 16, 18, 20, 22 or 24 hours after administration. In embodiments, provided herein are methods of treating TS including administering to a patient in need thereof a pharmaceutical composition including gaboxadol or a pharmaceutically acceptable salt thereof wherein the composition provides an in vivo plasma profile having a $AUC_{6-12}$ which is less than 100% of the administered dose and provides improvement in the patient for more than 6, 8, 10, 12, 14, 16, 18, 20, 22 or 24 hours after administration.

In embodiments, provided herein are methods of treating TS including administering to a patient in need thereof a first pharmaceutical composition including gaboxadol or a pharmaceutically acceptable salt thereof and a second pharmaceutical composition including gaboxadol or a pharmaceutically acceptable salt thereof wherein the second pharmaceutical composition provides an in vivo plasma profile having a mean $AUC_{0-\infty}$ of at least about 20% less than the first pharmaceutical composition.

In embodiments, provided herein are methods of treating tics including administering to a patient in need thereof a pharmaceutical composition including gaboxadol or a pharmaceutically acceptable salt thereof wherein the composition provides an in vivo plasma profile having a $C_{max}$ less than about 500 ng/ml. In embodiments, the composition provides improvement for more than 6 hours after administration to the patient.

In embodiments, the composition provides an in vivo plasma profile having a $C_{max}$ less than about, e.g., 450 ng/ml, 400 ng/ml 350 ng/ml, or 300 ng/ml and wherein the composition provides improvement in one or more symptoms of tics a day after administration. In embodiments, the composition provides an in vivo plasma profile having a $C_{max}$ less than about, e.g., 250 ng/ml, 200 ng/ml 150 ng/ml, or 100 ng/ml and wherein the composition provides improvement in one or more symptoms of tics a day after administration.

In embodiments, provided herein are methods of treating tics including administering to a patient in need thereof a pharmaceutical composition including gaboxadol or a pharmaceutically acceptable salt thereof wherein the composition provides an in vivo plasma profile having a $AUC_{0-\infty}$ of less than about 900 ng·hr/ml. In embodiments, the composition provides improvement in one or more symptoms of tics a day after administration. In embodiments, the compositions provide an in vivo plasma profile having a $AUC_{0-\infty}$ of less than about, e.g., 850 ng·hr/ml, 800 ng·hr/ml, 750 ng·hr/ml, or 700 ng·hr/ml and wherein the composition provides improvement in one or more symptoms of tics a day after administration. In embodiments, the composition provides improvement in one or more tics symptoms for more than 6 hours after administration.

In embodiments, provided herein are methods of treating tics including administering to a patient in need thereof a pharmaceutical composition including gaboxadol or a pharmaceutically acceptable salt thereof wherein the composition provides an in vivo plasma profile having a $AUC_{0-\infty}$ of less than about, e.g., 650 ng·hr/ml, 600 ng·hr/ml, 550 ng·hr/ml, 500 ng·hr/ml, or 450 ng·hr/ml. In embodiments, wherein the composition provides an in vivo plasma profile having a $AUC_{0-\infty}$ of less than about, e.g., 400 ng·hr/ml, 350 ng·hr/ml, 300 ng·hr/ml, 250 ng·hr/ml, or 200 ng·hr/ml. In embodiments, the composition provides an in vivo plasma profile having a $AUC_{0-\infty}$ of less than about, e.g., 150 ng·hr/ml, 100 ng·hr/ml, 75 ng·hr/ml, or 50 ng·hr/ml. In embodiments, the composition provides improvement symptoms of tics for more than, e.g., 4 hours, 6 hours, 8 hours, 10 hours, or 12 hours, after administration of the composition to the patient.

In embodiments, provided herein are methods of treating tics including administering to a patient in need thereof an amount of gaboxadol or a pharmaceutically acceptable salt thereof which provides an in vivo plasma profile having a $AUC_{6-12}$ which is less than 75% of the $C_{max}$ and provides improvement in the patient for more than 6, 8, 10, 12, 14, 16, 18, 20, 22 or 24 hours after administration. In embodiments, provided herein are methods of treating tics including administering to a patient in need thereof an amount of gaboxadol or a pharmaceutically acceptable salt thereof which provides an in vivo plasma profile having a $AUC_{6-12}$ which is less than 80% of the $C_{max}$ and provides improvement in the patient for more than 6, 8, 10, 12, 14, 16, 18, 20, 22 or 24 hours after administration. In embodiments, provided herein are methods of treating tics including administering to a patient in need thereof an amount of gaboxadol or a pharmaceutically acceptable salt thereof which provides an in vivo plasma profile having a $AUC_{6-12}$ which is less than 85% of the $C_{max}$ and provides improvement in the patient for more than 6, 8, 10, 12, 14, 16, 18, 20, 22 or 24 hours after administration. In embodiments, provided herein are methods of treating tics including administering to a patient in need thereof an amount of gaboxadol or a pharmaceutically acceptable salt thereof which provides an in vivo plasma profile having a $AUC_{6-12}$ which is less than 90% of the $C_{max}$ and provides improvement in the patient for more than 6, 8, 10, 12, 14, 16, 18, 20, 22 or 24 hours after administration. In embodiments, provided herein are methods of treating tics including administering to a patient in need thereof an amount of gaboxadol or a pharmaceutically acceptable salt thereof which provides an in vivo plasma profile having a $AUC_{6-12}$ which is less than 95% of the $C_{max}$ and provides improvement in the patient for more than 6, 8, 10, 12, 14, 16, 18, 20, 22 or 24 hours after administration. In embodiments, provided herein are methods of treating tics including administering to a patient in need thereof an amount of gaboxadol or a pharmaceutically acceptable salt thereof which provides an in vivo plasma profile having a $AUC_{6-12}$ which is less than 100% of the $C_{max}$ and provides improvement in the patient for more than 6, 8, 10, 12, 14, 16, 18, 20, 22 or 24 hours after administration.

In embodiments, provided herein are methods of treating tics including administering to a patient in need thereof a pharmaceutical composition including gaboxadol or a pharmaceutically acceptable salt thereof wherein the composition provides an in vivo plasma profile having a $AUC_{6-12}$ which is less than 75% of the $C_{max}$ and provides improvement in the patient for more than 6, 8, 10, 12, 14, 16, 18, 20, 22 or 24 hours after administration. In embodiments, provided herein are methods of treating tics including administering to a patient in need thereof a pharmaceutical composition including gaboxadol or a pharmaceutically acceptable salt thereof wherein the composition provides an in vivo plasma profile having a $AUC_{6-12}$ which is less than 80% of the $C_{max}$ and provides improvement in the patient for more than 6, 8, 10, 12, 14, 16, 18, 20, 22 or 24 hours after administration. In embodiments, provided herein are methods of treating tics including administering to a patient in need thereof a pharmaceutical composition including gaboxadol or a pharmaceutically acceptable salt thereof wherein the composition provides an in vivo plasma profile having a $AUC_{6-12}$ which is less than 85% of the $C_{max}$ and provides improvement in the patient for more than 6, 8, 10, 12, 14, 16, 18, 20, 22 or 24 hours after administration. In embodiments, provided herein are methods of treating tics including administering to a patient in need thereof a pharmaceutical composition including gaboxadol or a pharmaceutically acceptable salt thereof wherein the composition provides an in vivo plasma profile having a $AUC_{6-12}$ which is less than 90% of the $C_{max}$ and provides improvement in the patient for more than 6, 8, 10, 12, 14, 16, 18, 20, 22 or 24 hours after administration. In embodiments, provided herein are methods of treating tics including administering to a patient in need thereof a pharmaceutical composition including gaboxadol or a pharmaceutically acceptable salt thereof wherein the composition provides an in vivo plasma profile having a $AUC_{6-12}$ which is less than 95% of the $C_{max}$ and provides improvement in the patient for more than 6, 8, 10, 12, 14, 16, 18, 20, 22 or 24 hours after administration. In embodiments, provided herein are methods of treating tics including administering to a patient in need thereof a pharmaceutical composition including gaboxadol or a pharmaceutically acceptable salt thereof wherein the composition provides an in vivo plasma profile having a $AUC_{6-12}$ which is less than 100% of the $C_{max}$ and provides improvement in the patient for more than 6, 8, 10, 12, 14, 16, 18, 20, 22 or 24 hours after administration.

In embodiments, provided herein are methods of treating tics including administering to a patient in need thereof a pharmaceutical composition including gaboxadol or a pharmaceutically acceptable salt thereof wherein the composition provides an in vivo plasma profile having a $AUC_{6-12}$ which is less than 75% of the administered dose and provides improvement in the patient for more than 6, 8, 10, 12, 14, 16, 18, 20, 22 or 24 hours after administration. In embodiments, provided herein are methods of treating tics including administering to a patient in need thereof a pharmaceutical composition including gaboxadol or a pharmaceutically acceptable salt thereof wherein the composition provides an in vivo plasma profile having a $AUC_{6-12}$ which is less than 80% of the administered dose and provides improvement in the patient for more than 6, 8, 10, 12, 14, 16, 18, 20, 22 or 24 hours after administration. In embodiments, provided herein are methods of treating tics including administering to a patient in need thereof a pharmaceutical composition including gaboxadol or a pharmaceutically acceptable salt thereof wherein the composition provides an in vivo plasma profile having a $AUC_{6-12}$ which is less than 85% of the administered dose and provides improvement in the patient for more than 6, 8, 10, 12, 14, 16, 18, 20, 22 or 24 hours after administration. In embodiments, provided herein are methods of treating tics including administering to a patient in need thereof a pharmaceutical composition including gaboxadol or a pharmaceutically acceptable salt thereof wherein the composition provides an in vivo plasma profile having a $AUC_{6-12}$ which is less than 90% of the administered dose and provides improvement in the patient for more than 6, 8, 10, 12, 14, 16, 18, 20, 22 or 24 hours after administration. In embodiments, provided herein are methods of treating tics including administering to a patient in need thereof a pharmaceutical composition including gaboxadol or a pharmaceutically acceptable salt thereof wherein the composition provides an in vivo plasma profile having a $AUC_{6-12}$ which is less than 95% of the administered dose and provides improvement in the patient for more than 6, 8, 10, 12, 14, 16, 18, 20, 22 or 24 hours after administration. In embodiments, provided herein are methods of treating tics including administering to a patient in need thereof a pharmaceutical composition including gaboxadol or a pharmaceutically acceptable salt thereof wherein the composition provides an in vivo plasma profile having a $AUC_{6-12}$ which is less than 100% of the administered dose and provides improvement in the patient for more than 6, 8, 10, 12, 14, 16, 18, 20, 22 or 24 hours after administration.

In embodiments, provided herein are methods of treating tics including administering to a patient in need thereof a first pharmaceutical composition including gaboxadol or a pharmaceutically acceptable salt thereof and a second pharmaceutical composition including gaboxadol or a pharmaceutically acceptable salt thereof wherein the second pharmaceutical composition provides an in vivo plasma profile having a mean $AUC_{0-\infty}$ of at least about 20% less than the first pharmaceutical composition.

In embodiments, provided herein are methods of treating stuttering including administering to a patient in need thereof a pharmaceutical composition including gaboxadol or a pharmaceutically acceptable salt thereof wherein the composition provides an in vivo plasma profile having a $C_{max}$ less than about 500 ng/ml. In embodiments, the composition provides improvement for more than 6 hours after administration to the patient.

In embodiments, the composition provides an in vivo plasma profile having a $C_{max}$ less than about, e.g., 450 ng/ml, 400 ng/ml 350 ng/ml, or 300 ng/ml and wherein the composition provides improvement in one or more symptoms of stuttering a day after administration. In embodiments, the composition provides an in vivo plasma profile having a $C_{max}$ less than about, e.g., 250 ng/ml, 200 ng/ml 150 ng/ml, or 100 ng/ml and wherein the composition provides improvement in one or more symptoms of stuttering a day after administration.

In embodiments, provided herein are methods of treating stuttering including administering to a patient in need thereof a pharmaceutical composition including gaboxadol or a pharmaceutically acceptable salt thereof wherein the composition provides an in vivo plasma profile having a $AUC_{0-\infty}$ of less than about 900 ng·hr/ml. In embodiments, the composition provides improvement in one or more symptoms of stuttering a day after administration. In embodiments, the compositions provide an in vivo plasma profile having a $AUC_{0-\infty}$ of less than about, e.g., 850 ng·hr/ml, 800 ng·hr/ml, 750 ng·hr/ml, or 700 ng·hr/ml and wherein the composition provides improvement in one or more symptoms of stuttering a day after administration. In embodiments, the composition provides improvement in one or more stuttering symptoms for more than 6 hours after administration.

In embodiments, provided herein are methods of treating stuttering including administering to a patient in need thereof a pharmaceutical composition including gaboxadol or a pharmaceutically acceptable salt thereof wherein the composition provides an in vivo plasma profile having a $AUC_{0-\infty}$ of less than about, e.g., 650 ng·hr/ml, 600 ng·hr/ml, 550 ng·hr/ml, 500 ng·hr/ml, or 450 ng·hr/ml. In embodiments, wherein the composition provides an in vivo plasma profile having a $AUC_{0-\infty}$ of less than about, e.g., 400 ng·hr/ml, 350 ng·hr/ml, 300 ng·hr/ml, 250 ng·hr/ml, or 200 ng·hr/ml. In embodiments, the composition provides an in vivo plasma profile having a $AUC_{0-\infty}$ of less than about, e.g., 150 ng·hr/ml, 100 ng·hr/ml, 75 ng·hr/ml, or 50 ng·hr/ml. In embodiments, the composition provides improvement symptoms of stuttering for more than, e.g., 4 hours, 6 hours, 8 hours, 10 hours, or 12 hours, after administration of the composition to the patient.

In embodiments, provided herein are methods of treating stuttering including administering to a patient in need thereof an amount of gaboxadol or a pharmaceutically acceptable salt thereof which provides an in vivo plasma profile having a $AUC_{6-12}$ which is less than 75% of the $C_{max}$ and provides improvement in the patient for more than 6, 8, 10, 12, 14, 16, 18, 20, 22 or 24 hours after administration. In embodiments, provided herein are methods of treating stuttering including administering to a patient in need thereof an amount of gaboxadol or a pharmaceutically acceptable salt thereof which provides an in vivo plasma profile having a $AUC_{6-12}$ which is less than 80% of the $C_{max}$ and provides improvement in the patient for more than 6, 8, 10, 12, 14, 16, 18, 20, 22 or 24 hours after administration. In embodiments, provided herein are methods of treating stuttering including administering to a patient in need thereof an amount of gaboxadol or a pharmaceutically acceptable salt thereof which provides an in vivo plasma profile having a $AUC_{6-12}$ which is less than 85% of the $C_{max}$ and provides improvement in the patient for more than 6, 8, 10, 12, 14, 16, 18, 20, 22 or 24 hours after administration. In embodiments, provided herein are methods of treating stuttering including administering to a patient in need thereof an amount of gaboxadol or a pharmaceutically acceptable salt thereof which provides an in vivo plasma profile having a $AUC_{6-12}$ which is less than 90% of the $C_{max}$ and provides improvement in the patient for more than 6, 8, 10, 12, 14, 16, 18, 20, 22 or 24 hours after administration. In embodiments, provided herein are methods of treating stuttering including administering to a patient in need thereof an amount of gaboxadol or a pharmaceutically acceptable salt thereof which provides an in vivo plasma profile having a $AUC_{6-12}$ which is less than 95% of the $C_{max}$ and provides improvement in the patient for more than 6, 8, 10, 12, 14, 16, 18, 20, 22 or 24 hours after administration. In embodiments, provided herein are methods of treating stuttering including administering to a patient in need thereof an amount of gaboxadol or a pharmaceutically acceptable salt thereof which provides an in vivo plasma profile having a $AUC_{6-12}$ which is less than 100% of the $C_{max}$ and provides improvement in the patient for more than 6, 8, 10, 12, 14, 16, 18, 20, 22 or 24 hours after administration.

In embodiments, provided herein are methods of treating stuttering including administering to a patient in need thereof a pharmaceutical composition including gaboxadol or a pharmaceutically acceptable salt thereof wherein the composition provides an in vivo plasma profile having a $AUC_{6-12}$ which is less than 75% of the $C_{max}$ and provides improvement in the patient for more than 6, 8, 10, 12, 14, 16, 18, 20, 22 or 24 hours after administration. In embodiments, provided herein are methods of treating stuttering including administering to a patient in need thereof a pharmaceutical composition including gaboxadol or a pharmaceutically acceptable salt thereof wherein the composition provides an in vivo plasma profile having a $AUC_{6-12}$ which is less than 80% of the $C_{max}$ and provides improvement in the patient for more than 6, 8, 10, 12, 14, 16, 18, 20, 22 or 24 hours after administration. In embodiments, provided herein are methods of treating stuttering including administering to a patient in need thereof a pharmaceutical composition including gaboxadol or a pharmaceutically acceptable salt thereof wherein the composition provides an in vivo plasma profile having a $AUC_{6-12}$ which is less than 85% of the $C_{max}$ and provides improvement in the patient for more than 6, 8, 10, 12, 14, 16, 18, 20, 22 or 24 hours after administration. In embodiments, provided herein are methods of treating stuttering including administering to a patient in need thereof a pharmaceutical composition including gaboxadol or a pharmaceutically acceptable salt thereof wherein the composition provides an in vivo plasma profile having a $AUC_{6-12}$ which is less than 90% of the $C_{max}$ and provides improvement in the patient for more than 6, 8, 10, 12, 14, 16, 18, 20, 22 or 24 hours after administration. In embodiments, provided herein are methods of treating stuttering including administering to a patient in need thereof a pharmaceutical composition including gaboxadol or a pharmaceutically acceptable salt thereof wherein the composition provides an in vivo plasma profile having a $AUC_{6-12}$ which is less than 95% of the $C_{max}$ and provides improvement in the patient for more than 6, 8, 10, 12, 14, 16, 18, 20, 22 or 24 hours after administration. In embodiments, provided herein are methods of treating stuttering including administering to a patient in need thereof a pharmaceutical composition including gaboxadol or a pharmaceutically acceptable salt thereof wherein the composition provides an in vivo plasma profile having a $AUC_{6-12}$ which is less than 100% of the $C_{max}$ and provides improvement in the patient for more than 6, 8, 10, 12, 14, 16, 18, 20, 22 or 24 hours after administration.

In embodiments, provided herein are methods of treating stuttering including administering to a patient in need thereof a pharmaceutical composition including gaboxadol or a pharmaceutically acceptable salt thereof wherein the composition provides an in vivo plasma profile having a $AUC_{6-12}$ which is less than 75% of the administered dose and provides improvement in the patient for more than 6, 8, 10, 12, 14, 16, 18, 20, 22 or 24 hours after administration. In embodiments, provided herein are methods of treating stuttering including administering to a patient in need thereof a pharmaceutical composition including gaboxadol or a pharmaceutically acceptable salt thereof wherein the composition provides an in vivo plasma profile having a $AUC_{6-12}$ which is less than 80% of the administered dose and provides improvement in the patient for more than 6, 8, 10, 12, 14, 16, 18, 20, 22 or 24 hours after administration. In embodiments, provided herein are methods of treating stuttering including administering to a patient in need thereof a pharmaceutical composition including gaboxadol or a pharmaceutically acceptable salt thereof wherein the composition provides an in vivo plasma profile having a $AUC_{6-12}$ which is less than 85% of the administered dose and provides improvement in the patient for more than 6, 8, 10, 12, 14, 16, 18, 20, 22 or 24 hours after administration. In embodiments, provided herein are methods of treating stuttering including administering to a patient in need thereof a pharmaceutical composition including gaboxadol or a pharmaceutically acceptable salt thereof wherein the composition provides an in vivo plasma profile having a $AUC_{6-12}$ which is less than 90% of the administered dose and provides improvement in the patient for more than 6, 8, 10, 12, 14, 16, 18, 20, 22 or 24 hours after administration. In embodiments, provided herein are methods of treating stuttering including administering to a patient in need thereof a pharmaceutical composition including gaboxadol or a pharmaceutically acceptable salt thereof wherein the composition provides an in vivo plasma profile having a $AUC_{6-12}$ which is less than 95% of the administered dose and provides improvement in the patient for more than 6, 8, 10, 12, 14, 16, 18, 20, 22 or 24 hours after administration. In embodiments, provided herein are methods of treating stuttering including administering to a patient in need thereof a pharmaceutical composition including gaboxadol or a pharmaceutically acceptable salt thereof wherein the composition provides an in vivo plasma profile having a $AUC_{6-12}$ which is less than 100% of the administered dose and provides improvement in the patient for more than 6, 8, 10, 12, 14, 16, 18, 20, 22 or 24 hours after administration.

In embodiments, provided herein are methods of treating stuttering including administering to a patient in need thereof a first pharmaceutical composition including gaboxadol or a pharmaceutically acceptable salt thereof and a second pharmaceutical composition including gaboxadol or a pharmaceutically acceptable salt thereof wherein the second pharmaceutical composition provides an in vivo plasma profile having a mean $AUC_{0-\infty}$ of at least about 20% less than the first pharmaceutical composition.

In embodiments involving administration of a first pharmaceutical composition including gaboxadol or a pharmaceutically acceptable salt thereof, and a second pharmaceutical composition including gaboxadol or a pharmaceutically acceptable salt thereof, the first and/or the second pharmaceutical compositions may be administered once, twice, or three times daily, or every other day. In embodiments, the first or the second pharmaceutical composition is provided to the patient in the evening. In embodiments, the second pharmaceutical composition includes an amount of gaboxadol that is at least one third of the amount of gaboxadol provided in the first pharmaceutical composition. In embodiments, the second pharmaceutical composition includes an amount of gaboxadol that is at least half of the amount of gaboxadol provided in the first pharmaceutical composition.

In embodiments, the first or the second pharmaceutical composition is provided to the patient once in the evening and once in the morning. In embodiments, the total amount of gaboxadol or pharmaceutically acceptable salt thereof administered to a subject in a 24-hour period is 1 mg to 30 mg. In embodiments, the total amount of gaboxadol or a pharmaceutically acceptable salt thereof administered to a subject in a 24-hour period is 1 mg to 20 mg. In embodiments, the total amount of gaboxadol or a pharmaceutically acceptable salt thereof administered to a subject in a 24-hour period is 10 mg, 15 mg, or 20 mg. In embodiments, the total amount of gaboxadol or a pharmaceutically acceptable salt thereof administered to a subject in a 24-hour period is 20 mg.

In embodiments, the first and/or the second pharmaceutical compositions may be provided with immediate release, delayed release, extended release, or modified release profiles. The first and second pharmaceutical compositions may be provided at the same time or separated by an interval of time, e.g., 6 hours, 12 hours etc. In embodiments, the first and the second pharmaceutical compositions may be provided with different drug release profiles to create a two-phase release profile. For example, the first pharmaceutical composition may be provided with an immediate release profile and the second pharmaceutical composition may provide an extended release profile. In embodiments, one or both of the first and second pharmaceutical compositions may be provided with an extended release or delayed release profile. Such compositions may be provided as pulsatile formulations, multilayer tablets or capsules containing tablets, beads, granules, etc. In embodiments, the first pharmaceutical composition is an immediate release composition. In embodiments, the second pharmaceutical composition is an immediate release composition. In embodiments, the first and second pharmaceutical compositions are provided as separate immediate release compositions, e.g., tablets or capsules. In embodiments the first and second pharmaceutical compositions are provided 12 hours apart.

In embodiments, provided herein are methods of treating TS including administering to a patient in need thereof a first pharmaceutical composition including gaboxadol or a pharmaceutically acceptable salt thereof and a second pharmaceutical composition including gaboxadol or a pharmaceutically acceptable salt thereof wherein the second pharmaceutical composition provides an in vivo plasma profile having a mean $AUC_{0-\infty}$ of at least about, e.g., 25%, 30%, 35%, 40%, 45% or 50% less than the first pharmaceutical composition. In embodiments, the composition provides improvement in one or more symptoms of TS a day after administration. For example, the composition may provide improvement in one or more symptoms for more than about, e.g., 6 hours, 8 hours, 10 hours, or 12 hours after administration of the first and/or second pharmaceutical composition.

In embodiments, provided herein are methods of treating TS including administering to a patient in need thereof a first pharmaceutical composition including gaboxadol or a pharmaceutically acceptable salt thereof and a second pharmaceutical composition including gaboxadol or a pharmaceutically acceptable salt thereof wherein the second pharmaceutical composition provides an in vivo plasma profile having a mean $AUC_{0-\infty}$ of less than about 900 ng·hr/ml. In embodiments, the second pharmaceutical composition provides an in vivo plasma profile having a $AUC_{0-\infty}$ of less than about, e.g., 800 ng·hr/ml, 750 ng·hr/ml, 700 ng·hr/ml, 650 ng·hr/ml, or 600 ng·hr/ml. In embodiments, the second pharmaceutical composition provides an in vivo plasma profile having a $AUC_{0-\infty}$ of less than about, e.g., 550 ng·hr/ml, 500 ng·hr/ml, 450 ng·hr/ml, 400 ng·hr/ml, or 350 ng·hr/ml. In embodiments, the second pharmaceutical composition provides an in vivo plasma profile having a $AUC_{0-\infty}$ of less than about, e.g., 300 ng·hr/ml, 250 ng·hr/ml, 200 ng·hr/ml, 150 ng·hr/ml, or 100 ng·hr/ml. In embodiments, the first and second pharmaceutical composition are administered wherein the compositions provide improvement of next day functioning of the patient. In embodiments, the first pharmaceutical composition provides improvement in one or more symptoms for more than, e.g., 6 hours, 8 hours or 12 hours after administration of the first pharmaceutical composition.

In embodiments, provided herein are methods of treating TS including administering to a patient in need thereof a first pharmaceutical composition including gaboxadol or a pharmaceutically acceptable salt thereof and a second pharmaceutical composition including gaboxadol or a pharmaceutically acceptable salt thereof wherein the first composition provides an in vivo plasma profile with a $C_{max}$ that is more than about 50% greater than the $C_{max}$ provided by the administration of the second pharmaceutical composition. As used herein the $C_{max}$ provided by the administration of the second pharmaceutical composition may or may not include the plasma profile contribution of the first pharmaceutical composition. In embodiments, the administration of the second pharmaceutical composition does not include the plasma profile contribution of the first pharmaceutical composition. In embodiments, the first composition provides an in vivo plasma profile having a $C_{max}$ that is more than about e.g., 60%, 70%, 80%, or 90% greater than the $C_{max}$ provided by the administration of the second pharmaceutical composition.

In embodiments, provided herein are methods of treating tics including administering to a patient in need thereof a first pharmaceutical composition including gaboxadol or a pharmaceutically acceptable salt thereof and a second pharmaceutical composition including gaboxadol or a pharmaceutically acceptable salt thereof wherein the second pharmaceutical composition provides an in vivo plasma profile having a mean $AUC_{0-\infty}$ of at least about, e.g., 25%, 30%, 35%, 40%, 45% or 50% less than the first pharmaceutical composition. In embodiments, the composition provides improvement in one or more symptoms of tics or stuttering a day after administration. For example, the composition may provide improvement in one or more symptoms for more than about, e.g., 6 hours, 8 hours, 10 hours, or 12 hours after administration of the first and/or second pharmaceutical composition.

In embodiments, provided herein are methods of treating tics including administering to a patient in need thereof a first pharmaceutical composition including gaboxadol or a pharmaceutically acceptable salt thereof and a second pharmaceutical composition including gaboxadol or a pharmaceutically acceptable salt thereof wherein the second pharmaceutical composition provides an in vivo plasma profile having a mean $AUC_{0-\infty}$ of less than about 900 ng·hr/ml. In embodiments, the second pharmaceutical composition provides an in vivo plasma profile having a $AUC_{0-\infty}$ of less than about, e.g., 800 ng·hr/ml, 750 ng·hr/ml, 700 ng·hr/ml, 650 ng·hr/ml, or 600 ng·hr/ml. In embodiments, the second pharmaceutical composition provides an in vivo plasma profile having a $AUC_{0-\infty}$ of less than about, e.g., 550 ng·hr/ml, 500 ng·hr/ml, 450 ng·hr/ml, 400 ng·hr/ml, or 350 ng·hr/ml. In embodiments, the second pharmaceutical composition provides an in vivo plasma profile having a $AUC_{0-\infty}$ of less than about, e.g., 300 ng·hr/ml, 250 ng·hr/ml, 200 ng·hr/ml, 150 ng·hr/ml, or 100 ng·hr/ml. In embodiments, the first and second pharmaceutical composition are administered wherein the compositions provide improvement of next day functioning of the patient. In embodiments, the first pharmaceutical composition provides improvement in one or more symptoms for more than, e.g., 6 hours, 8 hours or 12 hours after administration of the first pharmaceutical composition.

In embodiments, provided herein are methods of treating tics including administering to a patient in need thereof a first pharmaceutical composition including gaboxadol or a pharmaceutically acceptable salt thereof and a second pharmaceutical composition including gaboxadol or a pharmaceutically acceptable salt thereof wherein the first composition provides an in vivo plasma profile with a $C_{max}$ that is more than about 50% greater than the $C_{max}$ provided by the administration of the second pharmaceutical composition. As used herein the $C_{max}$ provided by the administration of the second pharmaceutical composition may or may not include the plasma profile contribution of the first pharmaceutical composition. In embodiments, the administration of the second pharmaceutical composition does not include the plasma profile contribution of the first pharmaceutical composition. In embodiments, the first composition provides an in vivo plasma profile having a $C_{max}$ that is more than about e.g., 60%, 70%, 80%, or 90% greater than the $C_{max}$ provided by the administration of the second pharmaceutical composition.

In embodiments, provided herein are methods of treating stuttering including administering to a patient in need thereof a first pharmaceutical composition including gaboxadol or a pharmaceutically acceptable salt thereof and a second pharmaceutical composition including gaboxadol or a pharmaceutically acceptable salt thereof wherein the second pharmaceutical composition provides an in vivo plasma profile having a mean $AUC_{0-\infty}$ of at least about, e.g., 25%, 30%, 35%, 40%, 45% or 50% less than the first pharmaceutical composition. In embodiments, the composition provides improvement in one or more symptoms of stuttering a day after administration. For example, the composition may provide improvement in one or more symptoms for more than about, e.g., 6 hours, 8 hours, 10 hours, or 12 hours after administration of the first and/or second pharmaceutical composition.

In embodiments, provided herein are methods of treating stuttering including administering to a patient in need thereof a first pharmaceutical composition including gaboxadol or a pharmaceutically acceptable salt thereof and a second pharmaceutical composition including gaboxadol or a pharmaceutically acceptable salt thereof wherein the second pharmaceutical composition provides an in vivo plasma profile having a mean $AUC_{0-\infty}$ of less than about 900 ng·hr/ml. In embodiments, the second pharmaceutical composition provides an in vivo plasma profile having a $AUC_{0-\infty}$ of less than about, e.g., 800 ng·hr/ml, 750 ng·hr/ml, 700 ng·hr/ml, 650 ng·hr/ml, or 600 ng·hr/ml. In embodiments, the second pharmaceutical composition provides an in vivo plasma profile having a $AUC_{0-\infty}$ of less than about, e.g., 550 ng·hr/ml, 500 ng·hr/ml, 450 ng·hr/ml, 400 ng·hr/ml, or 350 ng·hr/ml. In embodiments, the second pharmaceutical composition provides an in vivo plasma profile having a $AUC_{0-\infty}$ of less than about, e.g., 300 ng·hr/ml, 250 ng·hr/ml, 200 ng·hr/ml, 150 ng·hr/ml, or 100 ng·hr/ml. In embodiments, the first and second pharmaceutical composition are administered wherein the compositions provide improvement of next day functioning of the patient. In embodiments, the first pharmaceutical composition provides improvement in one or more symptoms for more than, e.g., 6 hours, 8 hours or 12 hours after administration of the first pharmaceutical composition.

In embodiments, provided herein are methods of treating stuttering including administering to a patient in need thereof a first pharmaceutical composition including gaboxadol or a pharmaceutically acceptable salt thereof and a second pharmaceutical composition including gaboxadol or a pharmaceutically acceptable salt thereof wherein the first composition provides an in vivo plasma profile with a $C_{max}$ that is more than about 50% greater than the $C_{max}$ provided by the administration of the second pharmaceutical composition. As used herein the $C_{max}$ provided by the administration of the second pharmaceutical composition may or may not include the plasma profile contribution of the first pharmaceutical composition. In embodiments, the administration of the second pharmaceutical composition does not include the plasma profile contribution of the first pharmaceutical composition. In embodiments, the first composition provides an in vivo plasma profile having a $C_{max}$ that is more than about e.g., 60%, 70%, 80%, or 90% greater than the $C_{max}$ provided by the administration of the second pharmaceutical composition.

In embodiments involving administration of a first pharmaceutical composition including gaboxadol or a pharmaceutically acceptable salt thereof, and a second pharmaceutical composition including gaboxadol or a pharmaceutically acceptable salt thereof, the $T_{max}$ of the first pharmaceutical composition is less than 3 hours. In embodiments, the $T_{max}$ of the first pharmaceutical composition is less than 2.5 hours. In embodiments, the $T_{max}$ of the first pharmaceutical composition is less than 2 hours. In embodiments, the $T_{max}$ of the first pharmaceutical composition is less than 1.5 hours. In embodiments, the $T_{max}$ of the first pharmaceutical composition is less than 1 hour.

In embodiments, the first and/or the second pharmaceutical compositions contain sub therapeutic dosages. A sub therapeutic dosage of gaboxadol is an amount of gaboxadol or a pharmaceutically acceptable salt thereof that is less than the amount required for a therapeutic effect. In embodiments, a sub therapeutic dosage is an amount of gaboxadol or a pharmaceutically acceptable salt thereof that alone may not provide improvement in at least one symptom of TS, tics or stuttering, but is sufficient to maintain such improvement. In embodiments, the methods provide administering a first pharmaceutical composition that provides improvement in at least one symptom of TS, tics or stuttering, and a second composition that maintains the improvement. In embodiments, after administration of the first pharmaceutical composition, the second pharmaceutical composition may provide a synergistic effect to improve at least one symptom of TS, tics or stuttering. In embodiments the second pharmaceutical composition may provide a synergistic effect to improve at least one symptom of TS, tics or stuttering.

In embodiments, provided herein are methods of treating TS, tics or stuttering including administering to a patient in need thereof a pharmaceutical composition including a first pharmaceutical dosage including gaboxadol or a pharmaceutically acceptable salt thereof wherein the composition provides improvement for more than 6 hours after administration and a second pharmaceutical composition including a sub therapeutic dosage of gaboxadol or a pharmaceutically acceptable salt thereof.

Administration of the first and second pharmaceutical compositions may be separated by an interval of time to achieve long-term improvement in at least one symptom of TS, tics or stuttering. In embodiments, the first and second pharmaceutical composition may be administered 6 hours apart. In embodiments the first and second pharmaceutical composition may be administered 12 hours apart. In embodiments, the first and second pharmaceutical compositions may administered within, e.g., 6 hours, 12 hours, 18 hours, 24 hours etc. In embodiments, the first and second pharmaceutical compositions may administered separated by at least, e.g., 6 hours, 12 hours, 18 hours, 24 hours etc. In embodiments, improvement in at least one symptom of TS, tics or stuttering for more than 8 hours after administration to the patient is provided. In embodiments, improvement for more than about, e.g., 10 hours, 12 hours, 15 hours, 18 hours, 20 hours, or 24 hours after administration to the patient is provided. In embodiments, improvement in at least one symptom of TS, tics or stuttering for more than 8 hours after administration to the patient is provided. In embodiments, improvement for more than about, e.g., 10 hours, 12 hours, 15 hours, 18 hours, 20 hours, or 24 hours after administration to the patient is provided.

In embodiments, the first pharmaceutical composition and/or the second pharmaceutical composition include about 0.1 mg to about 40 mg gaboxadol or a pharmaceutically acceptable salt thereof. The amount of gaboxadol or a pharmaceutically acceptable salt thereof in the first pharmaceutical composition and the second pharmaceutical composition may be the same or different. In embodiments, the administration of the first and second pharmaceutical composition may provide a synergistic effect to improve at least one symptom of TS, tics or stuttering.

In embodiments, the first and/or the second pharmaceutical composition include 0.1 mg to 25 mg, 0.1 mg to 20 mg, 0.1 mg to 15 mg, 0.5 mg to 25 mg, 0.5 mg to 20 mg, 0.5 to 15 mg, 1 mg to 25 mg, 1 mg to 20 mg, 1 mg to 15 mg, 1.5 mg to 25 mg, 1.5 mg to 20 mg, 1.5 mg to 15 mg, 2 mg to 25 mg, 2 mg to 20 mg, 2 mg to 15 mg, 2.5 mg to 25 mg, 2.5 mg to 20 mg, 2.5 mg to 15 mg, 3 mg to 25 mg, 3 mg to 20 mg, or 3 mg to 15 mg gaboxadol or a pharmaceutically acceptable salt thereof.

In embodiments, the first and/or the second pharmaceutical composition include 5 mg to 15 mg, 5 mg to 10 mg, 4 mg to 6 mg, 6 mg to 8 mg, 8 mg to 10 mg, 10 mg to 12 mg, 12 mg to 14 mg, 14 mg to 16 mg, 16 mg to 18 mg, or 18 mg to 20 mg gaboxadol or a pharmaceutically acceptable salt thereof.

In embodiments, the first and/or the second pharmaceutical composition include 0.1 mg, 0.25 mg, 0.5 mg, 1 mg, 2.5 mg, 3 mg, 4 mg, 5 mg, 7 mg, 7.5 mg, 10 mg, 12.5 mg, 15 mg, 17.5 mg, 20 mg gaboxadol or a pharmaceutically acceptable salt thereof or amounts that are multiples of such doses. In embodiments, the first pharmaceutical compositions include 2.5 mg, 5 mg, 7.5 mg, 10 mg, 15 mg, or 20 mg gaboxadol or a pharmaceutically acceptable salt thereof. In embodiments, the second pharmaceutical compositions include 2.5 mg, 5 mg, 7.5 mg, 10 mg, 15 mg, or 20 mg gaboxadol or a pharmaceutically acceptable salt thereof.

In embodiments, the first pharmaceutical composition provides a dissolution of at least about 80% within the first 20 minutes of administration to a patient in need thereof. In embodiments, the first pharmaceutical composition provides a dissolution of at least about, e.g., 85%, 90% or 95% within the first 20 minutes of administration to a patient in need thereof. In embodiments, the first pharmaceutical composition provides a dissolution of at least 80% within the first 10 minutes of administration to a patient in need thereof.

In embodiments, provided herein are methods of treating TS including administering to a patient in need thereof a pharmaceutical composition including gaboxadol in combination with a second pharmaceutically active agent. In embodiments, provided herein are methods of treating tics including administering to a patient in need thereof a pharmaceutical composition including gaboxadol in combination with a second pharmaceutically active agent. In embodiments, provided herein are methods of treating stuttering including administering to a patient in need thereof a pharmaceutical composition including gaboxadol in combination with a second pharmaceutically active agent.

The second active agent may include typical and atypical neuroleptic agents such as risperidone, ziprasidone, haloperidol, pimozide and fluphenazine. The second active agent may include antihypertensive agents such as clonidine, guanfacine and propanolol. The second active agent may include anti-epileptic agents such as phenobarbital, phenytoin, lamotrigine, gabapentin, pregabalin, primidone, sodium valproate, and vigabatrin; anti-anxiety agents (anxiolytic agents) such as benzodiazepines including alprazolam, clonazepam, clobazepam, and diazepam; or anti-depressants such as amitriptyline, nortriptyline, doxepin, bupropion, sertraline, fluoxetine, citalopram, and escitalopram. The foregoing second active agents are representative and should not be considered a limiting.

Unless defined otherwise, all technical and scientific terms used herein have the same meanings as commonly understood by one of skill in the art to which the disclosure herein belongs.

The term "about" or "approximately" as used herein means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, up to 10%, up to 5%, and/or up to 1% of a given value. Alternatively, particularly with respect to biological systems or processes, the term can mean within an order of magnitude, preferably within 5-fold, and more preferably within 2-fold, of a value.

"Improvement" refers to the treatment of TS, tics or stuttering measured relative to at least one respective symptom.

"Improvement in one or more symptoms of TS, tics or stuttering a day after administration" refers to improvement wherein the beneficial effect of at least one symptom lasts over a period of time, e.g., 6 hours, 12 hours, 24 hours etc. "Improvement the next day" refers to improvement which occurs a day after administration of the active agent.

"PK" refers to the pharmacokinetic profile. $C_{max}$ is defined as the highest plasma drug concentration estimated during an experiment (ng/ml). $T_{max}$ is defined as the time when $C_{max}$ is estimated (min). $AUC_{0-\infty}$ is the total area under the plasma drug concentration-time curve, from drug administration until the drug is eliminated (ng·hr/ml). The area under the curve is governed by clearance. Clearance is defined as the volume of blood or plasma that is totally cleared of its content of drug per unit time (ml/min).

"Treating" or "treatment" refers to alleviating or delaying the appearance of clinical symptoms of a disease or condition in a subject that may be afflicted with or predisposed to the disease or condition, but does not yet experience or display clinical or subclinical symptoms of the disease or condition. In certain embodiments, "treating" or "treatment" may refer to preventing the appearance of clinical symptoms of a disease or condition in a subject that may be afflicted with or predisposed to the disease or condition, but does not yet experience or display clinical or subclinical symptoms of the disease or condition. "Treating" or "treatment" also refers to inhibiting the disease or condition, e.g., arresting or reducing its development or at least one clinical or subclinical symptom thereof. "Treating" or "treatment" further refers to relieving the disease or condition, e.g., causing regression of the disease or condition or at least one of its clinical or subclinical symptoms. The benefit to a subject to be treated may be statistically significant, mathematically significant, or at least perceptible to the subject and/or the physician. Nonetheless, prophylactic (preventive) and therapeutic (curative) treatment are two separate aspects of the disclosure herein.

"Pharmaceutically acceptable" refers to molecular entities and compositions that are "generally regarded as safe"—e.g., that are physiologically tolerable and do not typically produce an allergic or similar untoward reaction, such as gastric upset and the like, when administered to a human. In embodiments, this term refers to molecular entities and compositions approved by a regulatory agency of the federal or a state government, as the GRAS list under section 204(s) and 409 of the Federal Food, Drug and Cosmetic Act, that is subject to premarket review and approval by the FDA or similar lists, the U.S. Pharmacopeia or another generally recognized pharmacopeia for use in animals, and more particularly in humans.

"Composition", "pharmaceutical composition", "therapeutic composition", "formulation", "pharmaceutical formulation" are used interchangeably herein. "Composition", "pharmaceutical composition", "therapeutic composition", "formulation", "pharmaceutical formulation" encompass dosage forms. Dosage forms can encompass unit doses.

"Effective amount" or "therapeutically effective amount" means a dosage sufficient to alleviate one or more symptoms of a disorder, disease, or condition being treated, e.g., TS, tics or stuttering, or to otherwise provide a desired pharmacological and/or physiologic effect.

"Co-administered with", "in combination with", "a combination of", "administered along with", or "co-therapy", may be used interchangeably and mean that two or more agents are administered in the course of therapy. The agents may be administered together at the same time or separately in spaced apart intervals. The agents may be administered in a single dosage form or in separate dosage forms.

"Patient in need thereof" includes individuals that have been diagnosed TS, tics or stuttering. The methods may be provided to any individual including, e.g., wherein the patient is a neonate, infant, a pediatric patient (6 months to 12 years), an adolescent patient (age 12-18 years) or an adult (over 18 years). "Patient" and "subject" are used interchangeably herein.

EXAMPLES

The Examples provided herein are included solely for augmenting the disclosure herein and should not be considered to be limiting in any respect.

Example 1

The following Example provides the plasma concentration profiles and dose proportionality of gaboxadol monohydrate following single oral doses ranging from 2.5 to 20 mg. The absolute bioavailability of gaboxadol monohydrate capsules ranging from 2.5 to 20 mg is also assessed.

This study was composed of separate groups of 10 healthy adult subjects (at least 4 of each gender) who participated in a 6-period, double-blind, randomized, crossover study designed to access the dose proportionality and absolute bioavailability of 5 single oral doses of gaboxadol across the dose range of 2.5 to 20 mg. The order in which the subjects received the 5 single oral doses of gaboxadol (2.5; 5; 10; 15; and 20 mg) was randomized within Treatment Periods 1 through 5. Each subject was expected to complete all 6 treatment periods and there was a washout of at least 4 days between each treatment period.

Each oral dosing within Treatment Periods consisted of 2 capsules of test drug taken simultaneously at each scheduled dosing. The treatment designations for the orally administered study drugs were as follows: Treatment A—one 2.5 mg gaboxadol capsule and 1 matching placebo capsule; Treatment B—one 5 mg gaboxadol capsule and 1 matching placebo capsule; Treatment C—one 10 mg gaboxadol capsule and 1 matching placebo capsule; Treatment D—one 15 mg gaboxadol capsule and 1 matching placebo capsule; and Treatment E—20 mg gaboxadol (two 10 mg gaboxadol capsules). Subjects received their study drug after an overnight fast with 240 mL of water in the morning about 8:00 AM. Water was permitted ad libitum except within 1 hour prior to and after study drug administration. No food was allowed for 4 hours post dose.

For each subject in each treatment, plasma and urine samples were collected over 16 hours post-dosing for the determination of pharmacokinetic parameters (e.g., AUC, $C_{max}$, $T_{max}$, apparent $t_{1/2}$, cumulative urinary excretion, renal clearance, clearance, and steady-state volume of distribution, as appropriate). AUC and $C_{max}$ for gaboxadol were potency adjusted to facilitate comparison of pharmacokinetic data across studies. Table 1 provides the individual potency-adjusted pharmacokinetic parameters of gaboxadol following single oral doses (2.5, 5, 10, 15, and 20 mg).

TABLE 1

Pharmacokinetic parameters for gaboxadol following oral and IV administration

| Parameter | Geometric Mean (N = 10) | | | | | | |
|---|---|---|---|---|---|---|---|
| | 2.5 mg | 5 mg | 10 mg Oral | 10 mg I.V. | 15 mg | 20 mg | Slope (90% CI) [††] |
| $AUC_{0-\infty}$ (ng · hr/mL) | 90 | 171 | 346 | 380 | 539 | 669 | 0.98 (0.95, 1.01) |
| $C_{max}$ (ng/mL)[†] | 61 | 110 | 232 | 212 | 382 | 393 | 0.95 (0.88, 1.02) |
| $T_{max}$ (hr)[‡] | 0.5 | 0.6 | 0.5 | — | 0.5 | 0.6 | |
| Apparent $t_{1/2}$ (hr)[§] | 1.5 | 1.5 | 1.6 | 1.5 | 1.5 | 1.6 | |
| CL/F (mL/min)[ϑ] | 461 | 488 | 476 | 438 | 469 | 499 | |

TABLE 1-continued

Pharmacokinetic parameters for gaboxadol following oral and IV administration

| | Geometric Mean (N = 10) | | | | | | |
|---|---|---|---|---|---|---|---|
| Parameter | 2.5 mg | 5 mg | 10 mg Oral | 10 mg I.V. | 15 mg | 20 mg | Slope (90% CI) [††] |
| $F_e$ (%) | 43 | 45 | 53 | 53 | 50 | 53 | |
| $CL_R$ (mL/min) | 196 | 222 | 250 | 208 | 234 | 265 | |
| F (%) (90% CI)[#] | | | | 92% (0.86, 0.97) | | | |

[†]$C_{ooi}$ (ng/mL) for 10 mg. IV.
[‡]Median.
[§]Harmonic Mean.
[ϑ]CL (mL/min) for 10 mg IV.
[#]Bioavailability relative to 10 mg I.V. reference based on pooled dose-adjusted (to 10 mg) oral $AUC_{0-\infty}$ values.
[††] Dose proportionality assessment of oral treatments only.

Figure 2:
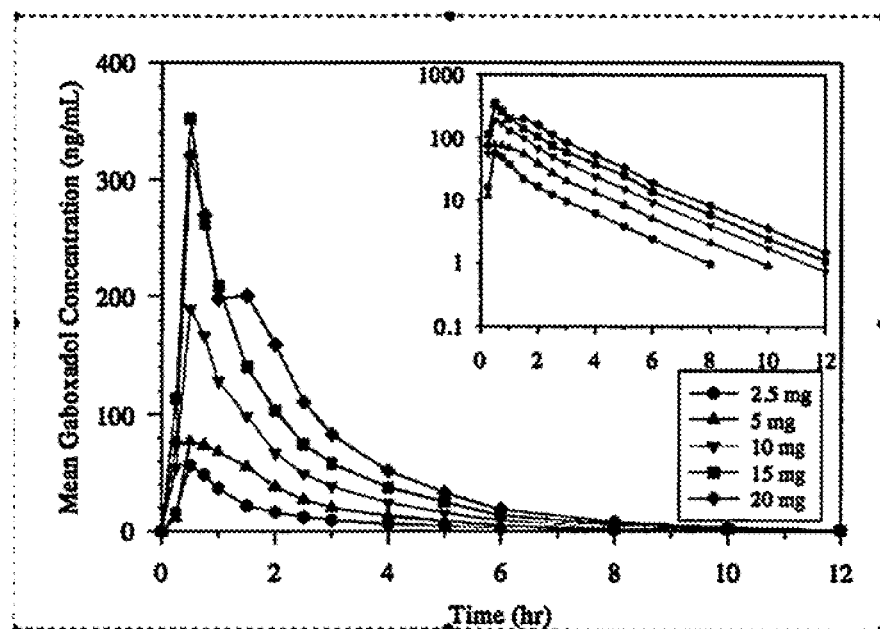
FIG. 2 shows the arithmetic mean plasma concentration-time profiles of gaboxadol following single oral doses (2.5, 5, 10, 15, and 20 mg) as described in Example 1.

FIG. 2 shows the arithmetic mean plasma concentration-time profiles of gaboxadol following single oral doses (2.5, 5, 10, 15, and 20 mg). The bioavailability of gaboxadol is approximately 92%. Plasma $AUC_{0-\infty}$ and $C_{max}$ of gaboxadol show dose proportional increases and appear to be linear over the entire dose range examined, from of 2.5 to 20 mg. The time to peak plasma concentrations ($T_{max}$ 30-60 min) and the half-life (t½ of 1.5 h) for gaboxadol appear to be independent of dose across the gaboxadol dose range of 2.5 to 20 mg. The excretion of gaboxadol is mainly via urine, where 96.5% of the dose is recovered; 75% is recovered within 4 hours after administration.

Example 2

Assessment of Residual Effects Resulting from Gaboxadol Administration

This study was a double blind, double-dummy, randomized, active- and placebo-controlled, single dose, 3-period crossover study, followed by an open-label, single-dose, single period study in healthy elderly male and female subjects. Subjects were randomized to each of 3 treatments (Treatments A, B, and C) to be administered in a crossover manner over the first 3 treatment periods. For Treatment A, subjects received a single dose of gaboxadol 10 mg; for Treatment B, subjects received a single dose of flurazepam 30 mg; and for Treatment C, subjects received a single dose of placebo. Doses were administered orally at bedtime on Day 1. Subjects were domiciled from early in the evening of dosing until ~36 hours post-dose (morning of Day 3) during each treatment period. The subjects who participated in treatment periods 1-3 participated in a fourth treatment period. In this period, a single dose of gaboxadol 10 mg (Treatment D) was administered orally in an open-label manner on the morning of Day 1 for PK of gaboxadol. There was at least a 14-day washout between the doses of consecutive treatment periods. Study participants included healthy, elderly male and female subjects between 65 and 80 years of age, with a Mini Mental Status 24, weighing at least 55 kg. All subjects received 10 mg gaboxadol monohydrate capsules and 30 mg flurazepam (provided as 2×15 mg capsules), matching placebo was provided for both gaboxadol and flurazepam.

The primary endpoints evaluated included pharmacodynamics (measurement of psychomotor performance, memory, attention and daytime sleepiness the following pm dosing), gaboxadol pharmacokinetics, and safety. Gaboxadol (single dose 10 mg) did not show residual effect 9 hours post-dose on the primary endpoints Choice Reaction Time and Critical Flicker Fusion, whereas the active reference Flurazepam (30 mg single dose) showed significant effect on the same tests. In addition, gaboxadol did not show any signs of residual effects on other measurements applied in the study (Multiple Sleep Latency Test (MSLT); Digit symbol substitution test (DSST), Tracking, Memory tests, Body Sway, and Leeds Sleep Evaluation Questionnaire).

Example 3

Prospective Assessment of the Efficacy of Gaboxadol in Patients with Tourette Syndrome This study is designed to determine whether gaboxadol leads to an improvement in Tourette syndrome. The primary objective of this study may be to evaluate the safety, tolerability and efficacy from Baseline to Week 6 and Week 12 of gaboxadol in subjects aged 7-17 with Tourette syndrome across different dose levels and in two dosing schedules. The following dosing schedules may be tested against placebo: (1) Once daily (o.d.): An evening dose, titrated to the target dose of 15 mg unless not tolerated; and (2) Twice daily (b.i.d.): Evening and morning doses titrated to the target doses of 15 mg evening dose and 10 mg morning dose unless not tolerated.

The Safety endpoints that relate to this study may include: (1) Frequency and severity of adverse events (AEs) and serious adverse events; (2) Vital signs (weight, blood pressure, temperature); (3) Laboratory parameters (electrolytes, lipids, glucose, liver and pancreas function tests, hematology, creatinine).

The secondary objective of this study may include the identification of a set of parameters that may best characterize the efficacy of gaboxadol in adult asthma subjects for subsequent efficacy trials. These tests may be administered at four full day site visits (Screening, Baseline, Interim and End of Treatment) by an appropriately trained professional to provide the test to an adult asthma patient. Assessments may be based, in part, on patient's perception of symptoms.

This study may include three treatment groups. For example, a total of approximately 75 subjects may be enrolled and at the completion of the study, there may be approximately 25 subjects in each of the three treatment groups: 1) single evening dose 2) morning and evening dose and 3) placebo. All subjects may be up-titrated to the target dose unless this target dose is not tolerated (titration conventions described below). All subjects may receive treatment for a maximum of 12 weeks at their optimal tolerated dose.

Doses may be progressively increased in 5 mg increments (active or placebo) to a target dose of 3 capsules evening dose in schedule A and B, and 2 capsules morning dose in schedule B. Each dose escalation may be performed after adequate tolerability has been assessed by caregiver and investigator. For example, treatment initiation at Day 1 with 1 capsule (active (Act) or placebo (Plc)) in the evening. Then target up-titration may begin at Day 3 (window+2 days): If no adverse event (AE) related to the study drug is observed by caregiver and/or the investigator, another capsule (active or placebo) is added in the evening. Again at Day 7 (window+2 days), Day 10 (window+2 days and Day 14 (window+2 days) if no AE related to the study drug is observed by caregiver and/or the investigator, another capsule (active or placebo) may be added in the morning. Table II below provides a graphic illustration of the titration schedule.

TABLE II

Titration Schedule

| Schedule/Time | | Days 1 to 2 | Days 3 to 6 | Days 7 to 9 | Days 10 to 13 | Day 14* |
|---|---|---|---|---|---|---|
| Schedule A | Evening | 5 mg 1 Capsule | 10 mg 2 Capsules | 15 mg 3 Capsules | 15 mg 3 Capsules | 15 mg 3 Capsules |
| | Morning | None | None | None | Placebo 1 Capsule | Placebo 2 Capsules |
| Schedule B | Evening | 5 mg 1 Capsule | 10 mg 2 Capsules | 15 mg 3 Capsules | 15 mg 3 Capsules | 15 mg 3 Capsules |
| | Morning | None | None | None | 5 mg 1 Capsule | 10 mg 2 Capsules |
| Schedule C | Evening | Placebo 1 Capsule | Placebo 2 Capsules | Placebo 1 Capsules | Placebo 3 Capsules | Placebo 3 Capsules |
| | Morning | None | None | None | Placebo 1 Capsule | Placebo 2 Capsules |

*To end of study treatment period

Slowed up-titration or delayed up-titration will be acceptable if tolerability does not allow immediate further dose-escalation at any of the above detailed days (3, 7, 10, 14). Down-titration in the case tolerability is not acceptable (e.g., somnolence, dizziness, change in behavior) after a previous up-titration step or during the course of the 12 week treatment, dose can be reduced to the previous level or even further. However, once a tolerable dose has been reached, it shall remain constant for the duration of the treatment period. Once a target dose is achieved the treatment may continue. For example, at Day 14: Earliest day the target dose can be reached (2 capsules in the morning and 3 in the evening) the subject may be kept stable until End of Treatment visit (week 12) unless intolerability requires down-titration.

All subjects will be screened for participation in the study up to 28 days prior to the first dose administration. Inclusion criteria may include one or more of the following: (1) Age ≥18 years, ≤40 years; (2) Must possess a clinical diagnosis of Tourette syndrome. Descriptive statistics may be used to summarize all primary and secondary endpoints as well as baseline variables, by treatment group. For continuous variables, n, number of missing values, mean, standard deviation, median, minimum, and maximum will be provided. For categorical variables, frequency and percentage will be presented for each category. Confidence intervals (CI) will be provided where meaningful. All CIs will be two-sided 95% confidence intervals.

Primary outcome measures: The Yale Global Tic Severity Scale (YGTSS) is the standard rating scale used to assess the effects of a new treatment on the symptoms of Tourette's Syndrome.

Secondary outcome measures: Safety will be assessed by monitoring and recording all Adverse Events (AE) and serious adverse events (SAE), regular monitoring of hematology, blood chemistry, and urine values, regular measurement of vital signs and the performance of a physical examination and an ECG. DuPaul ADHD rating scale-IV—This is a validated rating scale for the symptoms of attention deficit disorder. This is included because people with Tourette's often have attention deficit hyperactivity disorder (ADHD) as well. Child Yale-Brown Obsessive Compulsive Scale—This is validated rating scale which measures symptoms of obsessive-compulsive behaviors. People with Tourette's often also show symptoms of obsessive-compulsive behaviors. Children's Depression Inventory—The Children's Depression Inventory is a validate rating scale which measures signs of depression of in children. People with Tourette's often report feelings of depression. Clinical Global Impression-Improvement and Severity Scales-Clinical Global Impression Scales (improvement and severity) are validated rating scales that measure whether the treatment improves the symptoms of the disease (CGI-I) and whether the treatment reduces the severity of the disease (CGI-S).

Those skilled in the art will recognize, or be able to ascertain using no more than routine experimentation, many equivalents to the specific embodiments described herein. Such equivalents are intended to be encompassed by the claims.

What is claimed is:

1. A method of treating Tourette syndrome comprising administering to a patient in need thereof about 0.05 mg to about 30 mg gaboxadol or a pharmaceutically acceptable salt thereof, wherein the method provides improvement in one or more symptoms of Tourette syndrome in the patient.

2. The method of claim 1, wherein the improvement is provided for more than 6 hours after administration.

3. The method of claim 1, wherein the patient is administered a composition comprising about 1 mg to about 15 mg gaboxadol or a pharmaceutically acceptable salt thereof.

4. The method of claim 1, wherein the in vivo plasma profile of gaboxadol of the patient 6 hours after administration of the gaboxadol or pharmaceutically acceptable salt thereof is reduced by more than 50%.

5. The method of claim 1, wherein the $AUC_{6-12}$ of gaboxadol of the patient 6 hours after administration of the gaboxadol or pharmaceutically acceptable salt thereof is less than 75% of the administered dose.

6. The method of claim 1, wherein the method provides improvement in at least one symptom selected from the group consisting of simple tics, complex tics, and disabling tics.

7. The method of claim 6, wherein simple tics are selected from the group consisting of eye blinking, eye movements, facial grimacing, shoulder shrugging, head or shoulder jerking, repetitive throat-clearing, sniffing, grunting and barking sounds; complex tics are selected from the group consisting of facial grimacing combined with a head twist, facial grimacing combined with a shoulder shrug, sniffing objects, touching objects, hopping, jumping, bending, twisting, uttering words and uttering phrases; and disabling tics are selected from the group consisting of self harm tics, coprolalia and echolalia.

8. The method of claim 3, wherein the composition provides improvement in the patient for at least 12 hours.

9. The method of claim 1, wherein the method provides an in vivo plasma profile of gaboxadol comprising a $C_{max}$ less than about 400 ng/ml and wherein the method provides improvement in the patient for more than 6 hours after administration of the gaboxadol or a pharmaceutically acceptable salt thereof.

10. The method of claim 1, wherein the method provides an in vivo plasma profile of gaboxadol comprising a $AUC_{6-12}$ of less than about 900 ng·hr/ml and wherein the method provides improvement in the patient for more than 6 hours after administration of the gaboxadol or a pharmaceutically acceptable salt thereof.

11. A method of treating tics comprising administering to a patient in need thereof about 0.05 mg to about 30 mg gaboxadol or a pharmaceutically acceptable salt thereof, wherein the method provides improvement in one or more symptoms of the tics in the patient.

12. The method of claim 11, wherein the improvement is provided for more than 6 hours after administration.

13. The method of claim 11, wherein the patient is administered a composition comprising about 1 mg to about 15 mg gaboxadol or a pharmaceutically acceptable salt thereof.

14. The method of claim 11, wherein the in vivo plasma profile of gaboxadol of the patient 6 hours after administration of the gaboxadol or pharmaceutically acceptable salt thereof is reduced by more than 50%.

15. The method of claim 11, wherein the $AUC_{6-12}$ of gaboxadol of the patient 6 hours after administration of the gaboxadol or pharmaceutically acceptable salt thereof is less than 75% of the administered dose.

16. The method of claim 11, wherein the method provides improvement in at least one symptom selected from the group consisting of simple tics, complex tics, and disabling tics.

17. The method of claim 16, wherein simple tics are selected from the group consisting of eye blinking, eye movements, facial grimacing, shoulder shrugging, head or shoulder jerking, repetitive throat-clearing, sniffing, grunting and barking sounds; complex tics are selected from the group consisting of facial grimacing combined with a head twist, facial grimacing combined with a shoulder shrug, sniffing objects, touching objects, hopping, jumping, bending, twisting, uttering words and uttering phrases; and disabling tics are selected from the group consisting of self harm tics, coprolalia and echolalia.

18. The method of claim 13, wherein the composition provides improvement in the patient for at least 12 hours.

19. The method of claim 11, wherein the method provides an in vivo plasma profile of gaboxadol comprising a $C_{max}$ less than about 400 ng/ml and wherein the method provides improvement in the patient for more than 6 hours after administration of the gaboxadol or a pharmaceutically acceptable salt thereof.

20. The method of claim 11, wherein the method provides an in vivo plasma profile of gaboxadol comprising a $AUC_{6-12}$ of less than about 900 ng·hr/ml and wherein the method provides improvement in the patient for more than 6 hours after administration of the gaboxadol or a pharmaceutically acceptable salt thereof.

* * * * *